(12) United States Patent
Maguire et al.

(10) Patent No.: US 11,844,959 B2
(45) Date of Patent: *Dec. 19, 2023

(54) BLOOD-TISSUE SURFACE BASED RADIOSURGICAL RENAL TREATMENT PLANNING

(71) Applicant: Varian Medical Systems, Inc., Palo Alto, CA (US)

(72) Inventors: Patrick Maguire, Menlo Park, CA (US); Edward Gardner, San Jose, CA (US)

(73) Assignee: Varian Medical Systems, Inc., Palo Alto, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/482,027

(22) Filed: Sep. 22, 2021

(65) Prior Publication Data

US 2022/0008749 A1 Jan. 13, 2022

Related U.S. Application Data

(63) Continuation of application No. 16/273,932, filed on Feb. 12, 2019, now Pat. No. 11,154,725, which is a
(Continued)

(51) Int. Cl.
*A61N 5/10* (2006.01)
*A61B 90/00* (2016.01)
(Continued)

(52) U.S. Cl.
CPC ............ *A61N 5/103* (2013.01); *A61B 5/201* (2013.01); *A61B 90/37* (2016.02); *A61N 5/10* (2013.01);
(Continued)

(58) Field of Classification Search
CPC ........ A61N 5/10; A61N 5/103; A61N 5/1031; A61N 5/1037; A61N 5/1048;
(Continued)

(56) References Cited

U.S. PATENT DOCUMENTS 6,711,433 B1 * 3/2004 Geiger ................. G06T 11/008
378/98.12
6,889,695 B2 5/2005 Pankratov et al.
(Continued)

FOREIGN PATENT DOCUMENTS

CN 101267858 9/2008
CN 102481457 5/2012
(Continued)

OTHER PUBLICATIONS

European search report and search opinion dated Aug. 16, 2016 for EP Application No. 13867516.
(Continued)

*Primary Examiner* — Allen C. Ho
(74) *Attorney, Agent, or Firm* — Duane Morris LLP

(57) ABSTRACT

Devices, systems, and methods for planning radiosurgical treatments for neuromodulating a portion of the renovascular system may be used to plan radiosurgical neuromodulation treatments for conditions or disease associated with elevated central sympathetic drive. The renal nerves may be located and targeted at the level of the ganglion and/or at postganglionic positions, as well as preganglionic positions. Target regions include the renal plexus, celiac ganglion, the superior mesenteric ganglion, the aorticorenal ganglion and the aortic plexus. Planning of radiosurgical treatments will optionally employ a graphical representation of a blood/tissue interface adjacent these targets.

17 Claims, 25 Drawing Sheets

Related U.S. Application Data continuation of application No. 16/017,923, filed on Jun. 25, 2018, now abandoned, which is a continuation of application No. 14/752,442, filed on Jun. 26, 2015, now abandoned, which is a continuation of application No. PCT/US2013/077176, filed on Dec. 20, 2013.

(60) Provisional application No. 61/746,738, filed on Dec. 28, 2012.

(51) Int. Cl.
*A61B 5/20* (2006.01)
*A61B 18/00* (2006.01)

(52) U.S. Cl.
CPC ......... *A61N 5/1031* (2013.01); *A61N 5/1037* (2013.01); *A61N 5/1039* (2013.01); *A61N 5/1048* (2013.01); *A61N 5/1049* (2013.01); *A61N 5/1064* (2013.01); *A61N 5/1065* (2013.01); *A61N 5/1067* (2013.01); *A61N 5/1071* (2013.01); *A61N 5/1077* (2013.01); *A61N 5/1084* (2013.01); *A61B 2018/00511* (2013.01); *A61B 2090/374* (2016.02); *A61B 2090/378* (2016.02); *A61B 2090/3735* (2016.02); *A61B 2090/3762* (2016.02); *A61N 2005/1055* (2013.01); *A61N 2005/1061* (2013.01); *A61N 2005/1062* (2013.01); *A61N 2005/1072* (2013.01); *A61N 2005/1074* (2013.01)

(58) Field of Classification Search
CPC .......... A61N 5/1049; A61N 2005/1054; A61N 2005/1059; A61N 2005/1061; A61N 2005/1062; A61N 5/1064; A61N 5/1065; A61N 5/1067; A61N 5/1071; A61N 2005/1072; A61N 2005/1074; A61N 5/1077; A61N 5/1084; A61N 5/1039; A61N 2005/1052; A61N 2005/1055
USPC ............................. 378/62, 65; 382/130–132
See application file for complete search history.

(56) References Cited

U.S. PATENT DOCUMENTS

| | | | |
|---|---|---|---|
| 7,327,872 B2 | 2/2008 | Vaillant et al. | |
| 7,499,743 B2 | 3/2009 | Vass et al. | |
| 7,574,251 B2 | 8/2009 | Lu et al. | |
| 8,157,742 B2 | 4/2012 | Taylor | |
| 8,249,815 B2 | 8/2012 | Taylor | |
| 8,295,912 B2 | 10/2012 | Gertner | |
| 8,315,812 B2* | 11/2012 | Taylor | A61B 5/1118 382/128 |
| 8,515,527 B2 | 8/2013 | Vaillant et al. | |
| 8,548,778 B1 | 10/2013 | Hart et al. | |
| 8,554,490 B2 | 10/2013 | Tang et al. | |
| 8,824,752 B1 | 9/2014 | Fonte et al. | |
| 9,042,613 B2 | 5/2015 | Spilker et al. | |
| 9,072,894 B2 | 7/2015 | Chin et al. | |
| 9,087,147 B1 | 7/2015 | Fonte | |
| 9,183,764 B2 | 11/2015 | Sugimoto et al. | |
| 9,205,279 B2 | 12/2015 | Sumanaweera et al. | |
| 9,424,395 B2 | 8/2016 | Sankaran et al. | |
| 9,471,989 B2 | 10/2016 | O'Dell | |
| 9,504,435 B2 | 11/2016 | Bernhardt et al. | |
| 9,504,853 B2 | 11/2016 | Sumanaweera et al. | |
| 9,585,623 B2 | 3/2017 | Fonte et al. | |
| 9,839,483 B2* | 12/2017 | Sankaran | G06T 11/003 |
| 10,398,386 B2* | 9/2019 | Grady | A61B 5/742 |
| 10,974,069 B2 | 4/2021 | Maguire et al. | |
| 11,097,127 B2 | 8/2021 | Sumanaweera et al. | |
| 11,109,830 B2* | 9/2021 | De Backer | A61B 5/087 |
| 11,154,725 B2* | 10/2021 | Maguire | A61B 5/201 |
| 2011/0166407 A1 | 7/2011 | Sumanaweera et al. | |
| 2011/0166408 A1 | 7/2011 | Sumanaweera et al. | |
| 2012/0323233 A1 | 12/2012 | Maguire et al. | |
| 2015/0290472 A1 | 10/2015 | Maguire et al. | |

FOREIGN PATENT DOCUMENTS

| | | |
|---|---|---|
| CN | 102510735 | 6/2012 |
| WO | 2014105743 | 7/2014 |

OTHER PUBLICATIONS

International Search Report and Written Opinion of PCT Application No. PCT/US13/77176, dated Apr. 29, 2014. 16 pages.

Benedict et al., Sterotactic body radiation therapy: The report of AAPM Task Group 101, Med. Phys. 37(8), Aug. 2010, 0094-2405/2010/37(8)/4078/24, pp. 4078-4101 [online] [retrieved on Mar. 27, 2014]. Retrieved from the Internet: URL:http://www.aapm.org/pubs/reports/RPT_101.pdf.

* cited by examiner

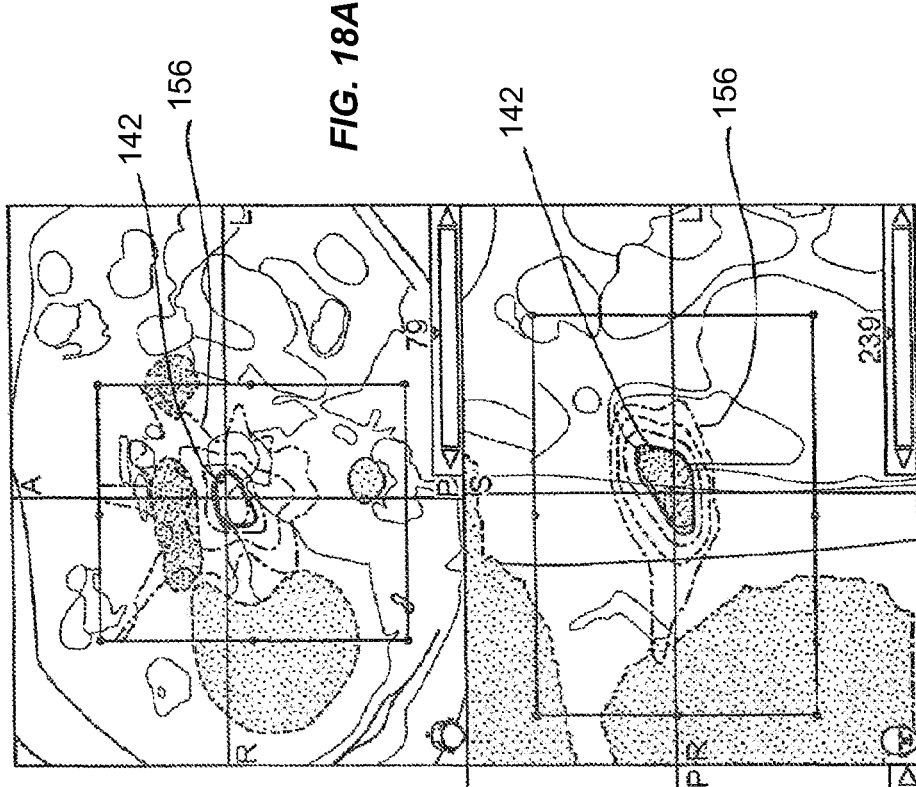
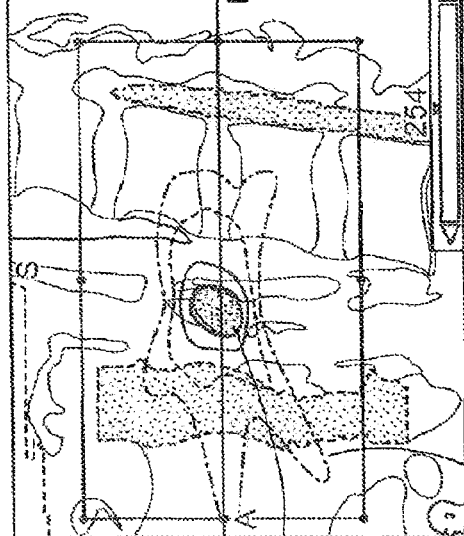
FIG. 18A
FIG. 18C
FIG. 18B

BLOOD-TISSUE SURFACE BASED RADIOSURGICAL RENAL TREATMENT PLANNING

CROSS-REFERENCES TO RELATED APPLICATIONS

This application is a continuation application of U.S. application Ser. No. 16/273,932 filed on Feb. 12, 2019 entitled "BLOOD-TISSUE SURFACE BASED RADIOSURGICAL RENAL TREATMENT PLANNING" issued as U.S. Pat. No. 11,154,725 issued on Oct. 26, 2021, which is a continuation of U.S. application Ser. No. 16/017,923, filed on Jun. 25, 2018, entitled "BLOOD-TISSUE SURFACE BASED RADIOSURGICAL RENAL TREATMENT PLANNING", which application is a continuation of U.S. application Ser. No. 14/752,442, filed Jun. 26, 2015, entitled "BLOOD-TISSUE SURFACE BASED RADIOSURGICAL RENAL TREATMENT PLANNING", which application claims priority to and is a continuation of PCT/US2013/077176, filed Dec. 20, 2013, entitled "BLOOD-TISSUE SURFACE BASED RADIOSURGICAL RENAL TREATMENT PLANNING", which claims the benefit under 35 U.S.C. § 119(e) of U.S. provisional application No. 61/746,738, filed Dec. 28, 2012, entitled "BLOOD-TISSUE SURFACE BASED RADIOSURGICAL RENAL TREATMENT PLANNING", the contents of which are incorporated herein by reference in their entireties.

BACKGROUND OF THE DISCLOSURE

Radiosurgery is a medical procedure that allows non-invasive treatment of tumors and other targets in the head, spine, abdomen, heart, and lungs. During radiosurgery, a series of beams of ionizing radiation are often directed from outside a patient so as to converge at a target region. The radiation beams often comprises MeV X-ray beams fired from different positions and orientations. The beam trajectories help limit radiation exposure to the intermediate and other collateral tissues, while the cumulative radiation dose at the target can alter or treat the tissue. The distribution of beams may be in three dimensions or two and further, the beams of ionizing radiation may be delivered to target tissue in a single procedure or multiple procedures. The CYBERKNIFE radiosurgical system (Accuray Inc.) and the TRILOGY radiosurgical system (Varian Medical Systems) are two known radiosurgical treatment systems.

Radiosurgical treatment of portions of a patient's renovascular system has been proposed as a treatment for hypertension. The link between hypertension and kidney function was uncovered when patients with end-stage renal disease underwent surgical removal of a kidney and thereafter showed a reduction in blood pressure and total systemic resistance. More specifically, it was discovered that hyperactivity of the nerves surrounding the renal arteries is linked to hypertension, the progression to chronic kidney disease, and heart failure. Since the discovery, renal denervation was proposed to reduce sympathetic outflow to the kidneys, increase urine output (naturiesis and diuresis) and thereby reduce rennin disease without adversely affecting other functions of the kidneys (e.g., glomerular filtration rate and/or renal blood flow).

Traditional treatments include ablation of the origin of the renal nerves in the sympathetic ganglia, pharmacological treatments, and device-based approaches. These approaches, however, each had various shortcomings. Ablating the origin of the renal nerves in the sympathetic ganglia has historically been considered very difficult. Pharmacologic assault on nerve functions is associated with systemic complications. Moreover, the sympathetic renal nerves arborize throughout the walls of the renal arteries and frustrate access thereto. As such, radiosurgical treatment has been proposed to deposit a sufficient ionizing radiation dose at a target of the renovascular system to ablate or modulate a portion of the renal nerves so as to reduce neural activity of the nerves, particularly the renal nerves located proximate to the renal arteries. The renovascular system may be located and targeted at the level of the ganglion and/or at postganglionic positions as well as at preganglionic positions.

Although there have been proposed advancements in radiosurgical renal denervation, it is still difficult and cumbersome to plan radiosurgical treatments for renal neuromodulation. In standard radiosurgical treatments of tumors and the like, computed tomography (CT) imaging provides a series of planar X-ray scans. For the X-rays adjacent a tumor, the planning physician draws a boundary of the target tissue, with the boundary being drawn on the scan traversing through the tumor and the boundary encompassing the tumor (and typically including some additional offset or margin of treated tissue for safety). As the tumor is typically contained within one organ (but may alternatively extend beyond the organ surface to an adjacent organ) the planned treatment boundary is fairy independent of tissue/tissue interface contours. Hence, the treatment plan is typically drawn up as a series of circles surrounding the tumor on each CT scan in which the tumor is visible.

It is difficult to draw an appropriate radiosurgical renovascular treatment plan for forming patterns on conventional planar CT scans using standard radiosurgical planning interfaces. A physician must evaluate the multiple CT scans, and draw appropriate lesion lines and/or circles representing a treatment plan at each planar slice of the target region of the renovascular system. The physician must be able to visualize desired treatment areas from each planar scan. While this appears to be a mere inconvenience, work in connection with the present invention indicates it is surprisingly difficult to efficiently establish an renovascular treatment plan using existing radio surgical treatment planning tools in light of the location and size of potential targets in the renovascular system.

In light of the above, the present inventors have determined that it is desirable to provide improved devices, systems, and methods for planning a radiosurgical treatment for alleviating renovascular hypertension. It would be particularly beneficial if these improvements were compatible with (and could be implemented by modification of) existing radiosurgical systems, ideally without significantly increasing the exposure of patients to incidental imaging radiation, without increasing the system costs so much as to make these treatments unavailable to many patients, without unnecessarily degrading the accuracy of the treatments, and/or without causing unnecessary collateral damage to the healthy tissues of the patient, including to endothelial tissues of the vasculature adjacent a target tissue.

SUMMARY OF THE DISCLOSURE

The present invention generally provides improved devices, systems, and methods for planning radiosurgical treatments for alleviating renovascular hypertension. Certain embodiments of the invention may provide a three-dimensional model of a renovascular target region which may help a physician better visualize the target region. A three-dimensional model of a blood/vessel boundary surface of a blood vessel adjacent to a renovascular nerve may be provided. Certain embodiments may receive input with reference to a radiation target which is offset from a three-dimensional model of blood/vessel boundary surface and/or may generate a three-dimensional model of an estimated target location by radially offsetting a distance from a blood/vessel boundary surface of a blood vessel adjacent to the renovascular target. Such embodiments may optionally receive input regarding a radiation target on an estimated target location surface. The input of the desired radiation target may be facilitated by snapping and extending an input target onto (or to a desired offset from) a three-dimensional model based on a user's input relative to a graphical representation of the three-dimensional model. Additional embodiments may receive an input target on a three-dimensional model of a blood/vessel boundary surface and may offset the input target a distance from the three-dimensional model of the blood/vessel boundary surface. Some embodiments provide a neural altering dose of radiation at an offset target site and a safe luminal dose of radiation at the blood/tissue boundary. Further some embodiments may allow a physician to better visualize the overall desired radiation target over the treatment area by displaying the inputted target relative to a surface model. Certain embodiments may display a dose cloud relative to the three-dimensional model to allow a physician to better visualize the radiation dose at portions of the target region according to the inputted treatment plan.

For example, in some exemplary embodiments a radiosurgical method for altering neural function of a patient body is provided. The method includes acquiring image data from a blood vessel adjacent to a nerve. A three dimensional model is generated from the image data by identifying a boundary surface between the blood vessel and blood flowing therein from the image data. An input identifying a radiation target, which is offset from the blood/vessel boundary surface, is received with reference to an image of the three-dimensional model. An irradiation treatment of the radiation target may then be planned so as to provide a neural function-altering dose of radiation at the target and a safe luminal dose of radiation at the blood/vessel boundary. Optionally, the nerve adjacent to the imaged blood vessel may be the renal plexus and the irradiation treatment may be configured to provide a decreasing dose gradient between the target and the blood/vessel boundary. The image data may be from an aorta or a renal artery. The radiation target may be offset from the blood/vessel boundary surface by an offset distance in a range from about 0.25 mm to about 6 mm. Additionally, the radiation target may vary longitudinally along the boundary surface and may vary within a range from about 0.5 mm to about 3.0 mm.

The method above may further include adjusting a pattern of beams of the radiation to compensate for movement of the blood vessel wall. The movement of the blood vessel wall may be due to a patient's respiration, a heartbeat or a bodily shift of the patient. The method may include outputting the ionizing radiation treatment pattern onto a plurality of slices of two-dimensional image data. In some embodiments input may be received on a display. The display may facilitate the input by snapping the input of the radiation target to a location relative the three-dimensional model. Further, embodiments may utilize a three dimensional model surface which is radially offset from the identified blood/vessel boundary surface and the display may facilitate the input by snapping the input of the radiation target onto the surface of the model.

In some embodiments the method may further include expanding a treatment pattern of intersecting radiation beams along a longitudinal axis of the blood/vessel boundary surface such that renal nerve activity is reduced so as to treat diseases and conditions related to hyperactivity of the sympathetic renal nerves, such as renal hypertension. The method may include generating an ionizing radiation treatment plan based on the treatment pattern and projecting a dose cloud to the three dimensional model based upon the treatment pattern so as to verify the dose of radiation along the blood/vessel boundary is sufficiently low to inhibit hyperplasia. The expected consequence of high doses of radiation on a large artery is thickening of the vessel wall and consequent stenosis of the vessel. The radiation target may include one or more annular circumferential segments. The nerve adjacent to the blood vessel may be one of a celiac ganglion, a superior mesenteric ganglion, an aorticorenal ganglion, nerves in the renal ostium region, and nerves in the renal artery branching region.

In other embodiments, a radiosurgical system for denervation of a patient body is provided. The system includes an image capture device for acquiring image data from a blood vessel adjacent to a nerve. A processor system can couple the image capture device to a display. The processor system can include a modeling module, an input module and a planning module. The modeling module may be configured for identifying a three dimensional boundary surface between the blood vessel and blood flowing therein from the image data. The modeling module can be configured for transmitting three dimensional model data to the display. The input module may receive user input data relative to the three dimensional model so as to identify a radiation target offset from the blood/vessel boundary surface. The planning module may be configured for planning a pattern of ionizing radiation treatment beams in response to the radiation target so as to reduce nerve activity within the nerve and to limit radiation along the blood/vessel boundary.

In some embodiments the image capture device may acquire image data from a blood vessel adjacent to the renal plexus. In certain embodiments, the planning module may be configured to plan the irradiation treatment so as to provide a decreasing dose between the target and the blood/vessel boundary. The image capture device may acquire image data from an aorta or a renal artery. The input module may receive user input data of a radiation target which is offset a distance within a range from about 0.25 mm to about 6 mm from the blood/vessel boundary surface. Further, the radiation target's offset distance may vary longitudinally along the boundary within a range from about 0.5 mm and 3.0 mm.

In further embodiments of the system, the planning module may be configured to output the ionizing radiation treatment plan for denervation of the adjacent nerve to a plurality of slices of two dimensional image data. A system may receive user input on the display and the display may facilitate the input by snapping the input of the ionizing radiation target relative to a location on the three dimensional model. The three dimensional model data may comprise a surface radially offset from the identified blood/vessel boundary surface and the display may facilitate the input by snapping the input of the radiation target onto the surface of the three dimensional model.

In certain embodiments of the system, the planning module is further configured to expand a treatment pattern of intersecting radiation beams along a longitudinal axis of the blood/vessel boundary surface such that renal nerve activity is reduced so as to treat hypertension. The planning module may be configured to generate an ionizing radiation treatment plan based upon the user input and may project a dose cloud to the three dimensional model based upon the treatment pattern so as to verify the dose of radiation along the blood/vessel boundary is sufficiently low to inhibit hyperplasia. The radiation target may include one or more annual circumferential segments. The image capture device may acquire image data from a blood vessel adjacent to one of a celiac ganglion, a superior mesenteric ganglion, an aorticorenal ganglion, nerves in the renal ostium region, and nerves in the renal artery branching region.

In some embodiments, a non-transitory computer readable medium with computer executable instruction stored thereon for developing a radiosurgical renal denervation treatment plan is provided. The computer readable medium may include instructions for acquiring image data from a blood vessel adjacent to a nerve. The computer readable medium instructions may generate a three dimensional model by identifying a boundary surface between the blood vessel and blood flowing therein from the image data. Input regarding a radiation target with reference to an image of the three dimensional model may be received. The received radiation target input may be offset from the blood/vessel boundary surface. An irradiation treatment of the radiation target may be planned so as to provide a neural function-altering dose of radiation at the target and a safe luminal dose of radiation at the blood/vessel boundary. A ionizing radiation treatment plan may optionally be generated based on the user input and a dose cloud may be projected on the three dimensional model based on the treatment plan if desired. In some embodiments, the surface may be a layer between the epithelial cell layer and the outer edge of the blood vessel adventitia. In certain embodiments, the dose cloud may be evaluated to ensure the safe luminal dose of radiation at the blood/vessel boundary.

BRIEF DESCRIPTION OF THE DRAWINGS

FIG. 10A is a representation of a blood/vessel boundary surface and FIG. 10B is an estimated target location surface in accordance with FIG. 8;

FIGS. 18A-18E is an axial slice of a generated surface of FIG. 15 with the dose cloud and the treatment lines shown thereon;

DETAILED DESCRIPTION OF THE INVENTION

The present invention generally provides improved devices, systems, and methods for planning radiosurgical treatments for neuromodulating a portion of the renovascular system. The embodiments herein may be used to plan radiosurgical neuromodulation treatments for conditions or disease associated with elevated central sympathetic drive, including renovascular hypertension, heart failure, chronic kidney disease, insulin resistance, diabetes, metabolic syndrome, sleep apnea, atrial fibrillation, and/or dyspnea. Additionally, embodiments of the present invention detailed herein and variations thereof may be used to plan radiosurgical renal neuromodulation of various target regions. The renal nerves may be located and targeted at the level of the ganglion and/or at postganglionic positions, as well as preganglionic positions. Target regions include the renal plexus, celiac ganglion, the superior mesenteric ganglion, the aorticorenal ganglion and the aortic plexus.

It should be understood that reference to the singular, as in a renal artery, renal nerves about a renal artery, kidney, etc., encompasses both the singular and plural, and vice versa. It is further to be understood that while embodiments may be described herein with reference to renal nerves, the teachings herein and variations thereof may also be applicable to the renal ganglia and/or the aortic renal ganglia in general. Indeed, the teachings herein and variations thereof are applicable to a wide variety of devices, systems and/or methods that utilize ionizing radiation to partially or completely block neurological communication between one or both kidneys of a patient and a patient's central nervous system, thereby reducing hypertension or the like, including robotic radiosurgical systems, gantry-type radiosurgical systems, and the like. Thus, while preferred embodiments have been described, the details may be changed without departing from the invention, which is defined by the claims.

Figure 1A:
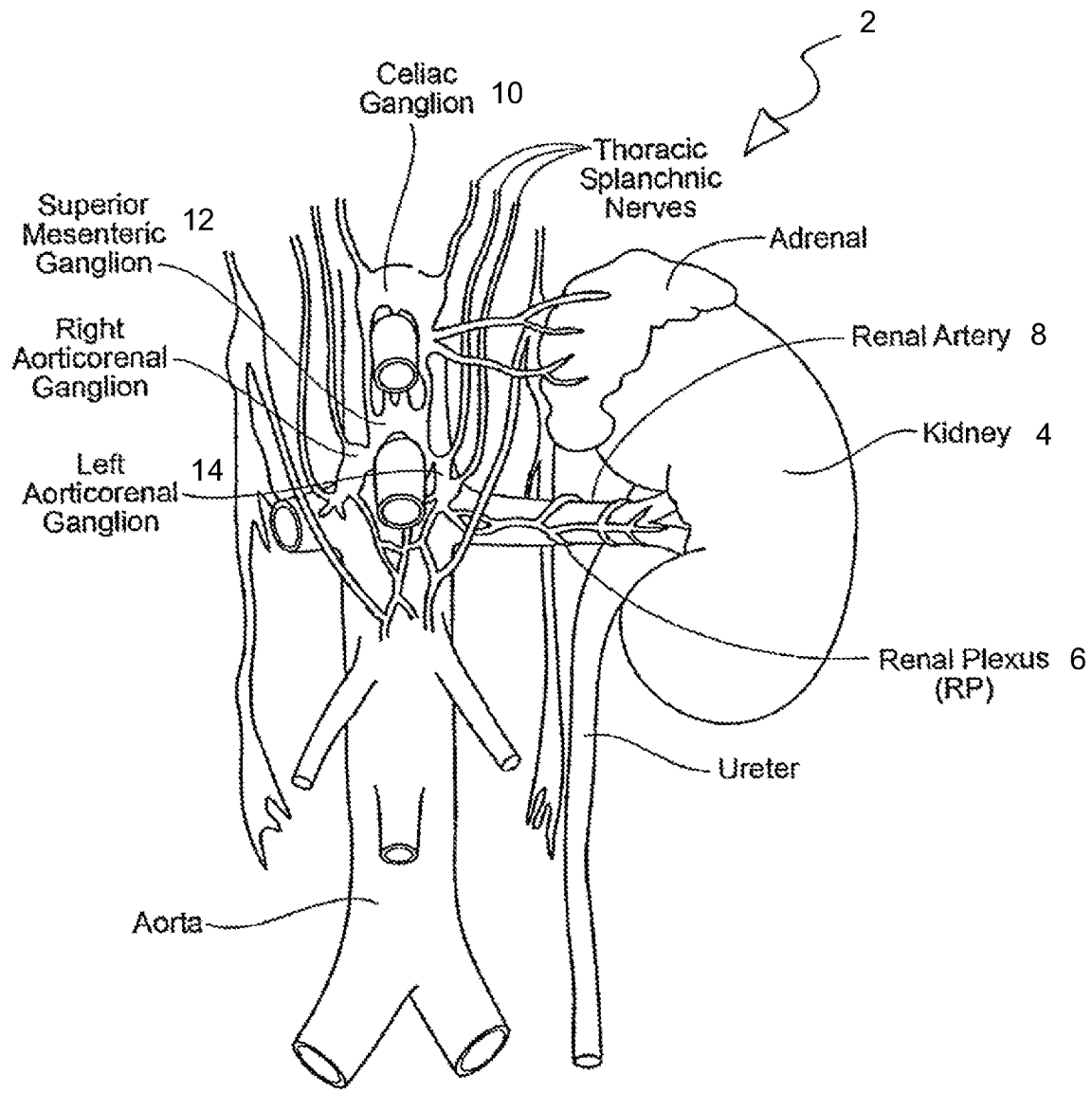
FIGS. 1A-1B illustrate portions of the renovascular structure to which embodiments of the present invention may be applicable.
Figure 1B:
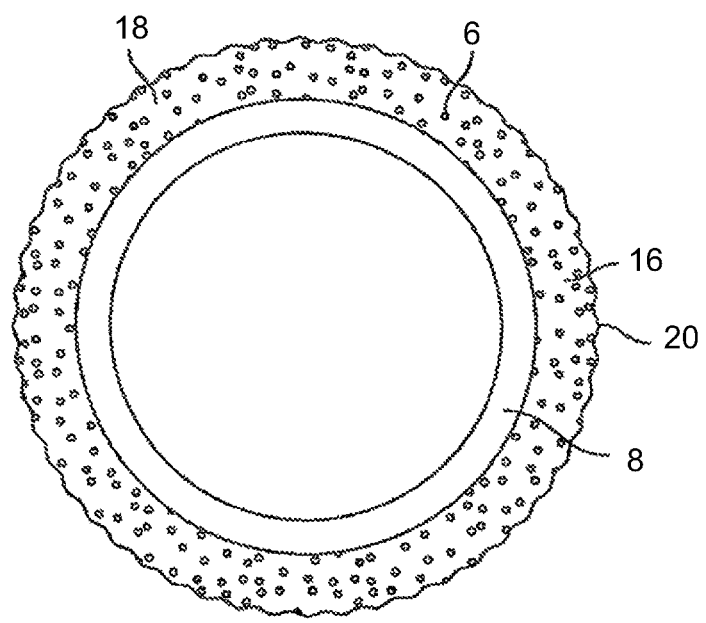

FIG. 1A illustrates a portion of the renovascular structure 2. As may be seen in FIG. 1A, the kidney 4 is innervated by the renal plexus (RP) 6, which is intimately associated with the renal artery 8. The renal plexus 6 is an autonomic plexus that surrounds the renal artery 8 and is embedded within or adjacent to the adventitia of the renal artery 8. The renal plexus 6 extends along the renal artery 8 until it arrives at the substance of the kidney 4. Fibers contributing to the renal plexus 6 arise from the celiac ganglion 10, the superior mesenteric ganglion 12, the aorticorenal ganglion 14 and the aortic plexus. The renal plexus 6, also referred to as the renal nerve or nerves, is predominantly comprised of sympathetic components. There is no (or at least very little) parasympathetic innervation of the kidney 4. FIG. 1B depicts a conceptual unscaled cross-sectional view of the renal artery 8 and renal nerves 6. The renal nerves 6 are surrounded by membrane 16 located in periarterial space 18. The boundary of membrane 20 is conceptually depicted. In an exemplary embodiment of the present invention, the ionizing radiation treatment plan at least provides radiation doses sufficient to reduce neural activity by partially enveloping renal nerves 6.

Figure 2:
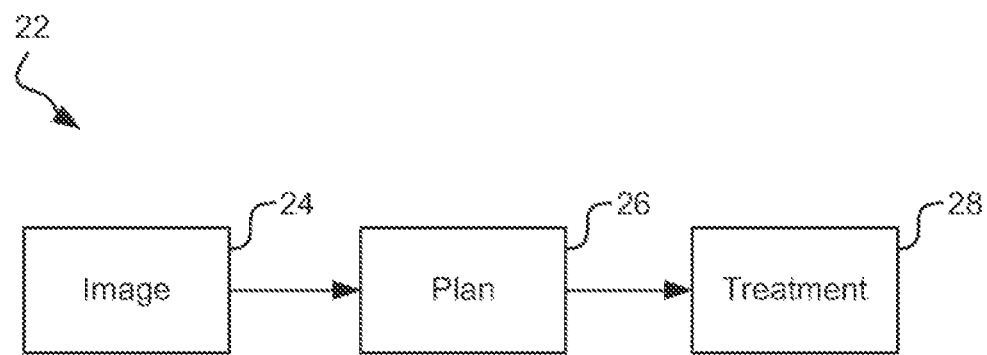
FIG. 2 is a flowchart representing a method of radiosurgical treatment according to the embodiments.

FIG. 2 provides an exemplary flow chart 22 which represents a method used for radiosurgical treatment according to embodiments of the present invention. The target tissues are first imaged 24 by a medical imaging modality, and then a plan 26 can be prepared for treatment of the tissue at the target site. After completion of plan 26, radiosurgical treatment 28 of the renal nerve may be initiated according to plan 26.

The internal tissues are imaged 24 for planning purposes, typically using a remote imaging modality such as a computed tomography (CT), magnetic resonance imaging (MRI), ultrasound imaging, X-ray imaging, optical coherence tomography, a combination of these, or other imaging modalities. Note that the tissue structure which will actually be targeted for radiation remodeling need not necessarily be visible in the image, for example, when sufficiently contrasting surrogate structures are visible in the image data to identify the target tissue location. The imaging used in many embodiments will include a time sequence of three-dimensional tissue volumes, with the time sequence typically spanning one or more movement cycles (such as a cardiac or heartbeat cycle, a respiration or breathing cycle, and/or the like). In exemplary embodiments, the image data comprises a series of CT slices through a blood vessel adjacent to the target renal nerve so as to provide volumetric or three-dimensional image data. The time series of three-dimensional blood vessel images are preferably acquired at times that are distributed throughout the heartbeat cycle so that the image planning data effectively comprises a time series of three-dimensional image datasets providing information regarding the motion of the blood vessel tissues during the cardiac cycle.

Based on the imaging data obtained from imaging 24, a plan 26 can be prepared for treatment of the tissue at the target site. Embodiments herein are directed to systems and methods that aid in development of plan 26 which may be used with existing or newly developed imaging 24 and treatment 28. One advantage of the plan 26 defined herein is that it may be used with existing imaging, such as the CT imaging described above, and with conventional radiosurgical planning tools, such as the MULTIPLAN planning tool (Accuray, Inc.). Imaging, for example, may take the forms described above or other forms. In exemplary embodiments a conventional series of image slices (e.g. CT slices) through a blood vessel adjacent to the renal nerve is utilized so as to provide volumetric or three-dimensional image data. Treatment 28 may be conventional or modified, and one embodiment is described in concurrently filed U.S. Patent Application No. 61/483,962 entitled, "Renovascular Treatment Device, System, and Method for Radiosurgically Alleviating Hypertension" (Attorney Docket No. 88587-782065), the full disclosure of which is incorporated herein by reference.

Treatment plan 26 typically comprises a target region and a series of radiation beams which intersect within the target region. The radiation dose within the target tissue should be at least sufficient to provide the desired lesions or renal neuromodulation. For example, the radiation dose may comprise ablative or sub-ablative doses of ionizing radiation. The dose will be sufficient to inhibit or reduce sympathetic activity of the renal nerve. Radiation dosages outside the target tissue will preferably decrease with a relatively steep gradient so as to inhibit excessive damage to collateral tissues, with radiation dosages in specified sensitive and/or critical tissue structures often being maintained below a desired maximum threshold to avoid deleterious side effects. For example, treatment plan 26 may be configured or adjusted to minimize radiation exposure at the endothelium. Further, radiation exposure at the blood vessel lumen may be minimized so as to minimize the chances of blood occlusion within the blood vessel adjacent to the target nerve.

Figure 3:
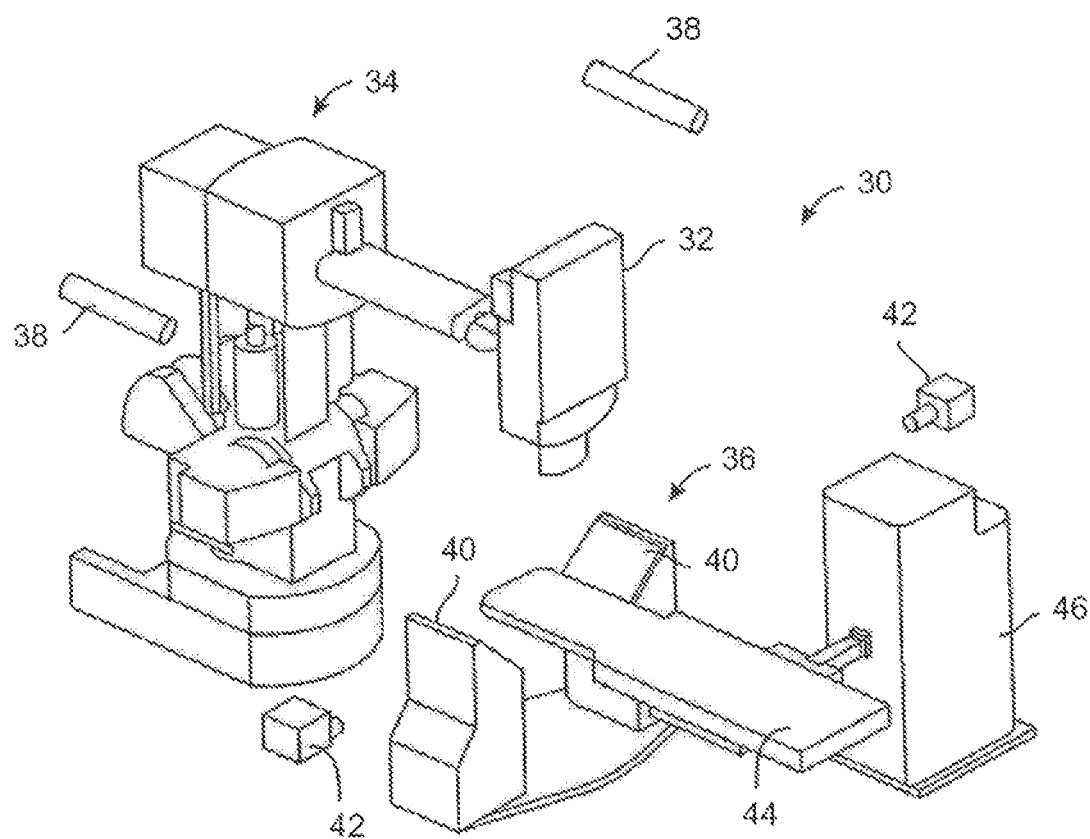
FIG. 3 illustrates an exemplary modified stereotactic radiosurgery system that may be utilized with embodiments.

Treatment 28 may utilize known radiation delivery systems to treat a patient according to plan 26. As an example, an exemplary modified CYBERKNIFE stereotactic radiosurgery system 30 is illustrated in FIG. 3. Radiosurgery system 30 includes a lightweight linear accelerator 32 mounted to a robotic arm 34. An image guidance system 36 includes biplane diagnostic X-ray sources 38 and image detectors 40 so as to enhance registration between the robotic arm 34 and the target site. As the tissues in the target region may not present a high-contrast image, image guidance system 36 may use image processing techniques to identify the location of one or more surrogate structures, with the surrogates typically including a high-contrast natural tissue structure (such as a bone or the like) or an artificial implanted fiducial marker that moves in correlation with the target tissue. Target tracking may also make sure of one or more surface image cameras 42, particularly for identifying pulsatile movement of blood vessels adjacent to renal nerves. Cameras 42 may monitor high-contrast fiducial markers placed relative to the target nerve. A patient support 44 is moveably supported by an alignment arm 46 so as to facilitate bringing the patient (and treatment site) into alignment with the robotic arm 34.

Figure 4:
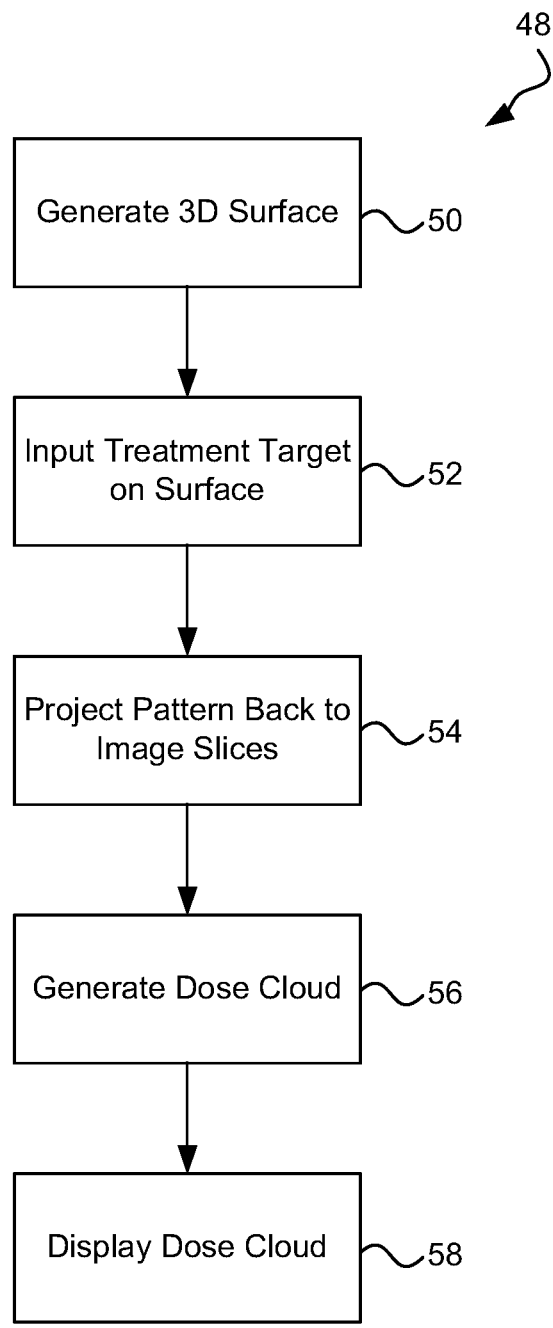
FIG. 4 is a flowchart broadly describing treatment planning according to embodiments of the present invention.
Figure 5A:
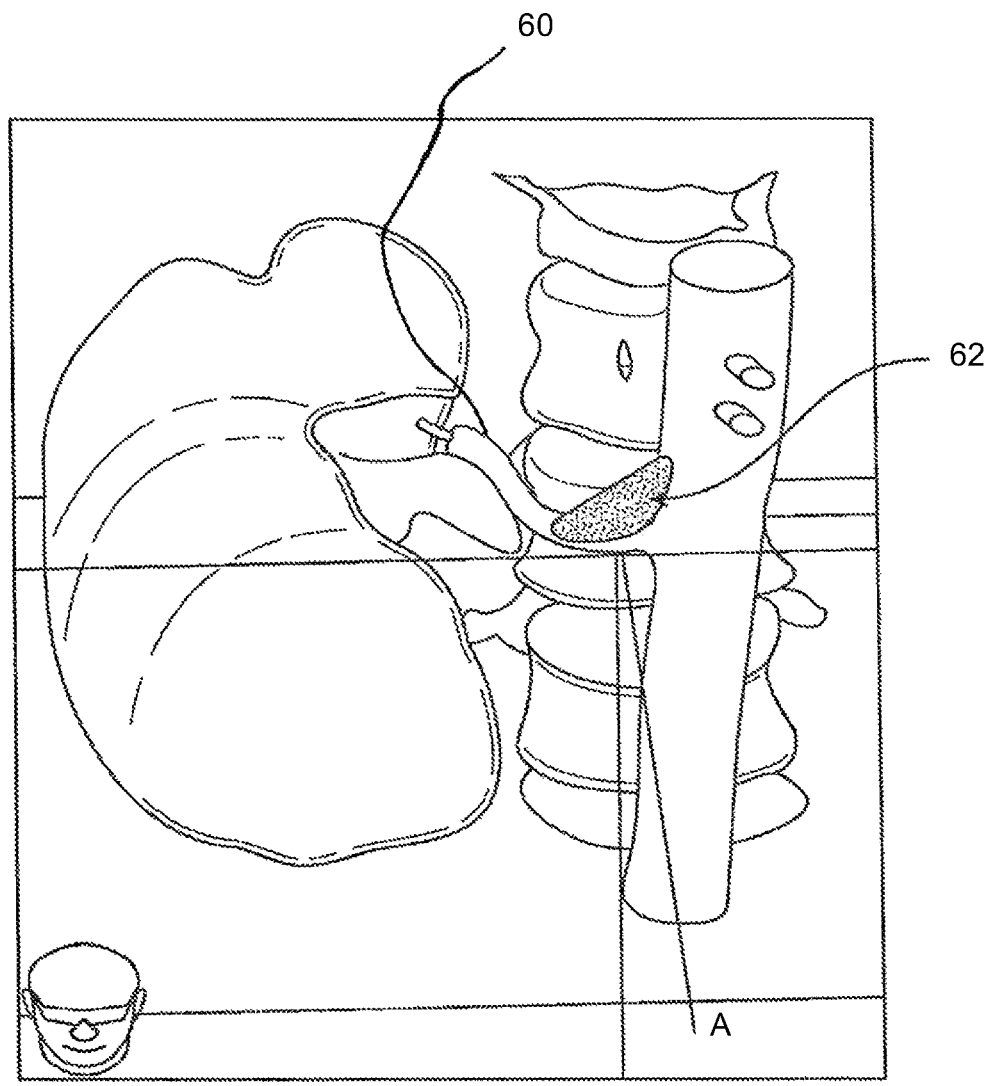
FIGS. 5A-5C depict exemplary target treatment regions with reference to anatomical structure according to an exemplary embodiment of the present invention.

Referring now to FIGS. 4 and 5A, FIG. 4 describes an exemplary planning flowchart 48 and FIG. 5A illustrates portions of the exemplary planning process. A modeling module generates 50 a three dimensional model of a surface 60, generally from CT slices of a blood vessel adjacent to a target nerve, although other imaging data may be used. In the example shown in the drawings, the surface 60 is of a portion of the renovascular system. A user interface or input module allows the system user to input 52 a desired radiation treatment pattern 62 with reference to the model. The desired radiation treatment pattern 62 is at an offset distance from the blood/tissue boundary of a blood vessel adjacent to the radiation target. The offset distance allows a neural function-altering dose of radiation at the radiation target and a safe luminal dose of radiation at the adjacent blood/vessel boundary.

At 54, the series of boundaries generated by the desired radiation pattern 62 may be projected back onto the individual CT scan slices, which then may be transferred to a conventional radiosurgical planning tool. Thus, the input to the conventional radiosurgical tools is generally the same as the input in prior methods (i.e. boundaries defined on individual CT scan slices). However, as described in the background of this disclosure, prior methods required a surgeon to draw on each individual slice. In contrast, methods and systems herein generate the desired treatment pattern 62 relative to the three dimensional model of the surface 60.

Figure 5C:
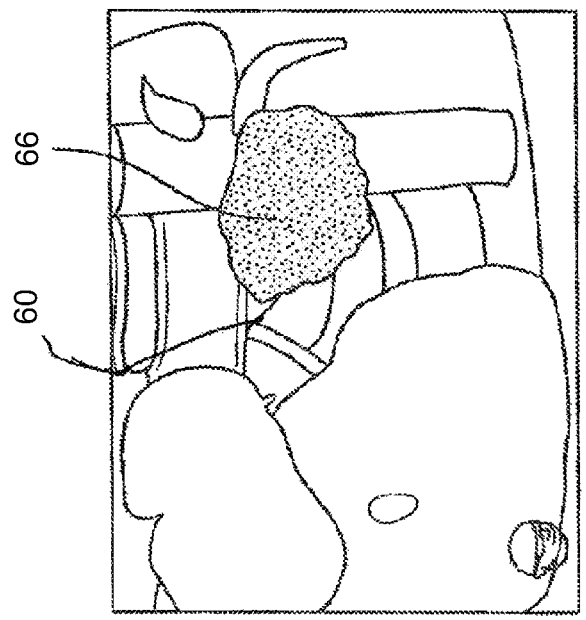
Figure 5B:
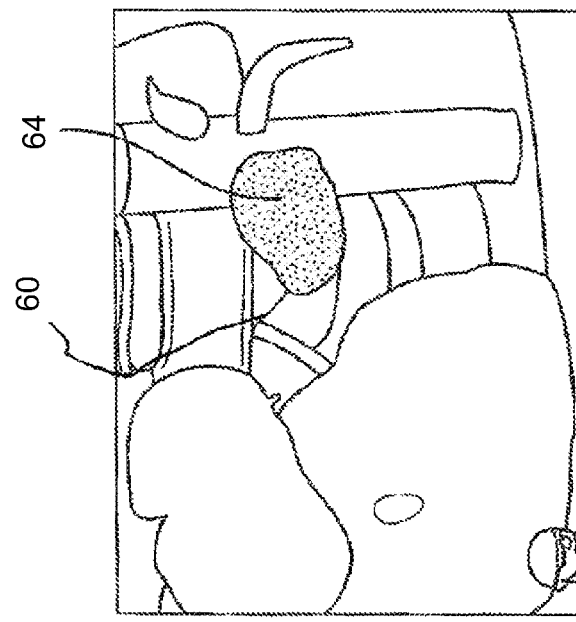

In some embodiments, as described below, a visualization of a dose cloud 64 and 66 (FIG. 5B-5C) may be provided for displaying on the surface 60. The dose cloud 64 in FIG. 5B depicts, in a quasi-three dimensional manner, the outer boundaries of a 20 Gy dose cloud. Dose cloud 66 in FIG. 5C illustrates the outer boundaries of a 10 Gy dose cloud. The dose cloud may be received 56 as an output treatment indication by a conventional radiosurgical tool and, in accordance with embodiments, may be displayed 58, for example, as an isodose contour on the surface 60. As with the desired treatment pattern 62, the dose cloud 64 and 66 may be used in part of generating or approving the plan 26 (FIG. 2).

To generate a surface 60 if the blood/vessel boundary surface of a blood vessel adjacent to a target nerve, a modeling module may be configured for identifying a three dimensional boundary surface between a blood vessel and blood flowing therein from the image data. An image contrast agent may be introduced during the image acquisition step 24 so that the inner surface of the blood vessel may be more easily identified from the image data. Thus, there is a clear demarcation between the tissue and the blood, allowing for a more precise definition of the blood/vessel boundary surface 60.

For example, if the target nerves include the renal plexus, the modeling module may identify the boundary surface between the renal artery and the blood. A model of the blood/vessel boundary surface of the renal artery may then be used for planning a radiosurgical treatment of the renal plexus. Although the surface has been described as the blood/tissue interface of the renal artery adjacent to the renal plexus, it will be appreciated that this example is illustrative and variations and modifications are possible. For instance, surface 60 may be the blood/tissue interface of other blood vessels adjacent to other renovascular nerves. Alternative embodiments may employ a surface radially offset a distance from the identified blood/tissue boundary. The offset distance may correspond to an estimated location of the target nerve. For example, the renal nerves may be offset from the blood/tissue boundary of the renal artery at a range from about 0.25 mm to about 6 mm. An embodiment may provide a surface radially offset 2 mm from the blood/tissue boundary of the renal artery as an estimate of a renal nerve target location. Further, the offset distance from the identified blood/tissue boundary surface may vary longitudinally along the boundary. Other nerve targets may range at an offset distance from about 0.5 mm to about 3.0 mm.

Figure 6:
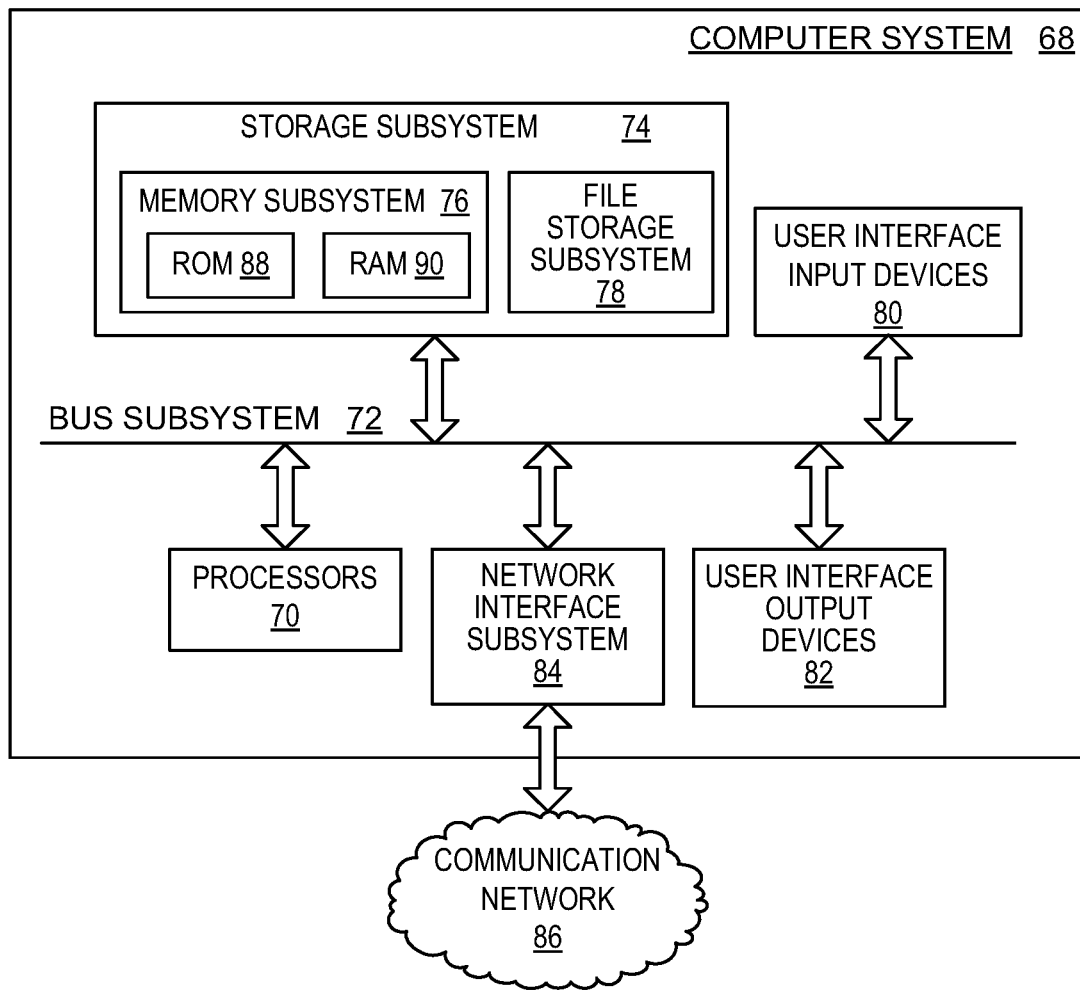
FIG. 6 is a block diagram of a computer system that may be utilized with embodiments herein.

Embodiments herein may utilize computer-implemented methods for generating the three dimensional surface 50, indicating a desired treatment pattern 52, providing the dose cloud 56, and/or operate the methods or functions of the systems described herein. To this end, FIG. 6 is a simplified block diagram of an exemplary computer system 68 that may be utilized in embodiments described herein. The computer system 68 typically includes at least one processor 70 which communicates with a number of peripheral devices via a bus subsystem 72. These peripheral devices may include a storage subsystem 74, comprising a memory subsystem 76 and a file storage subsystem 78, user interface input devices 80, user interface output devices 82, and a network interface subsystem 84. Network interface subsystem 84 provides an interface to a communication network 86 for communication with other imaging devices, databases, or the like.

The processor 70 performs the operations of the computer system 68 using execution instructions stored in the memory subsystem 76 in conjunction with any data input from an operator. Such data can, for example, be input through user interface input devices 80, such as the graphical user interface. Thus, processor 70 can include an execution area into which execution instructions are loaded from memory. These execution instructions will then cause processor 70 to send commands to the computer system 68. Although described as a "processor" in this disclosure, the functions of the processor may be performed by multiple processors in one computer or distributed over several computers.

User interface input devices 80 may include a keyboard, pointing devices such as a mouse, trackball, touch pad, or graphics tablet, a scanner, foot pedals, a joy stick, a touch-screen incorporated into the display, audio input devices such as voice recognition systems, microphones, and other types of input devices. In general, use of the term "input device" is intended to include a variety of conventional and proprietary devices and ways to input information into the computer system 68. Such input devices will often be used to download a computer executable code from a computer network or a tangible storage media embodying steps or programming instructions for any of the methods of the present invention.

User interface output devices 82 may include a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide non-visual display such as via audio output devices. In general, use of the term "output device" is intended to include a variety of conventional and proprietary devices and ways to output information from the computer system to a user.

Storage subsystem 74 stores the basic programming and data constructs that provide the functionality of the various embodiments. For example, database and modules implement the functionality of embodiments described herein may be stored in storage subsystem 74. These software modules are generally executed by processor 70. In a distributed environment, the software modules may be stored in a memory or a plurality of computer systems and executed by processors of the plurality of computer systems and executed by processors of the plurality of computer systems. Storage subsystem 74 typically comprises memory subsystems 76 and file storage subsystem 78.

Memory subsystems 76 typically includes a number of memories including a read only memory (ROM) 88 in which fixed instructions are stored and main random access memory (RAM) 90 for storage of instructions and data during program execution. File storage subsystem 78 provides persistent (non-volatile) storage for program and data files, and may include a hard disk drive, a floppy disk drive along with associated removable media, a Compact Digital Read Only Memory (CD-ROM) drive, an optical drive, DVD, CD-R, CD-RW, or removable media cartridges or disks. One or more of the drives may be located at remote locations on other connected computers at other sites coupled to the computer system. The databases and modules implementing the functionality of the present invention may also be stored by file storage subsystem 78.

Bus subsystem 72 provides a mechanism for letting the various components and subsystems of the computer system communicate with each other as intended. The various subsystems and components of the computer system need not be at the same physical location but may be distributed at various locations within a distributed network. Although bus subsystem 72 is shown schematically as a single bus, alternate embodiments of the bus subsystem may utilize multiple buses.

The computer system or computing device 68 itself can be of varying types include a personal computer, a portable computer, a workstation, a computer terminal, a network computer, a module in a display unit, a mainframe, or any other data processing system. Due to the ever-changing nature of computers and networks, the description of the computer system or computing device 68 depicted in FIG. 6 is intended only as a specific example for purposes of illustrating one embodiment of the present invention. Many other configurations of the computer system are possible having more or fewer components than the computer system or computing device 68 depicted in FIG. 6.

Figure 7:
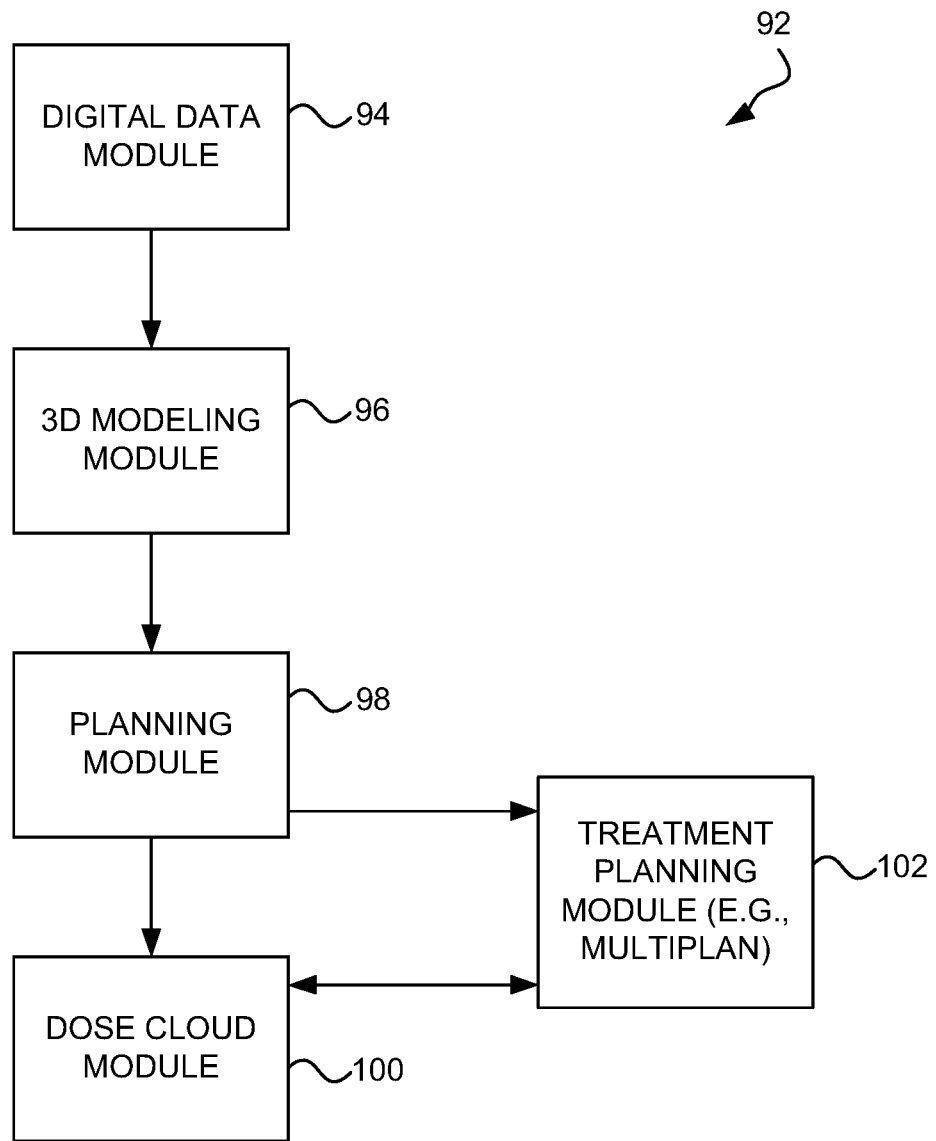
FIG. 7 schematically illustrates a plurality of modules that may carry out embodiments of the present invention.

FIG. 7 schematically illustrates a plurality of modules 92 that may carry out embodiments of the present invention. The modules 92 may be software modules, hardware modules or a combination thereof. If the modules 92 are software modules, the modules will be embodied on a computer readable medium and processed by processor 70.

A digital data module 94 receives CT volume or other diagnostic images and, if not already digitized, creates a digital data file of the images. A 3-D modeling module 96 builds a finite element or solid model of the desired surface from the digital data file. Such 3-D modeling modules are known, and example implementation details are provided below, along with a description of FIG. 8. However, briefly described, the 3-D modeling module 96 process the slices of the CT volume and creates a finite element or solid model of the surface of interest, projected as the surface 60 (FIGS. 5A-5C) For ease of reference, as used from this point forward, the "surface 60" refers to the 3-D model of the surface of interest. As set forth above, surface 60 may be in the blood/tissue boundary of a blood vessel adjacent to a renovascular nerve. Further, surface 60 may be a radially offset distance from the blood/tissue boundary so as to provide an estimated nerve target location.

The surface 60 may be shown, for example on a display for the computing device 68, and may be manipulated by a user, for example via the user interface input device 80 so as to see a desired orientation, cross section, or other desired view. Panning and yaw and pitch movement may be provided as well.

A planning module 98 permits a user of the system to generate the treatment plan 62 (FIG. 5A). The planning module 98 may also project the treatment plan back onto the CT slices.

A dose cloud module 100 may receive or generate the dose cloud 64 and 66. An example implementation of the dose cloud module 100 is set forth below, for example with the discussions of FIGS. 16 and 19.

The dose cloud module 100 and the 3-D modeling module 96 may be utilized with a standard treatment planning module 102. An example of such a treatment planning module is the MULTIPLAN treatment module, although other treatment modules may be used.

Figure 8:
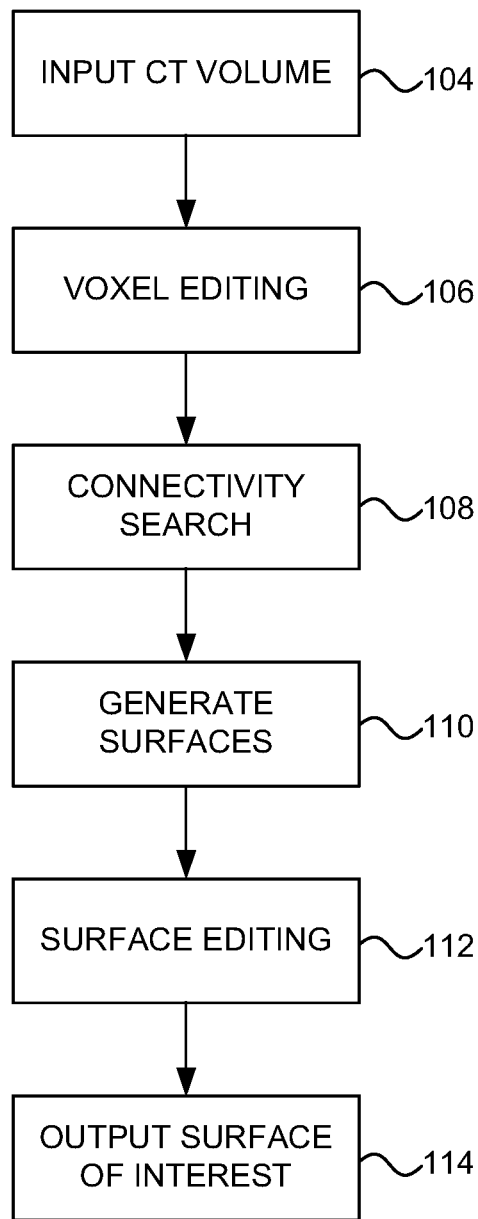
FIG. 8 is a flow chart representing a method of generating a three dimensional model of a surface of interest in accordance with an embodiment.

FIG. 8 is a flowchart representing a method of generating a surface of interest, e.g., the surface 60, in accordance with an embodiment. At 104, the information regarding the CT volume is input, for example via the module 94. This input may be, for example, a CT volume generated to accentuate the tissue-blood boundary information provided for each CT slice. In the examples described herein, the tissue-blood boundary is the boundary between the blood and the inner surface a blood vessel adjacent to a renovascular nerve and that boundary is accentuated by, for example, adding a contrasting agent to the blood. The boundary between the blood (including the added contrast) and the blood vessel tissue in each slice of the CT data can be segmented in one, some, or all of the volumetric data sets associated with the cardiac cycle phases. The segmented regions can be stacked or assembled together to form the surface 60.

At 106 to 112, examples are provided of smoothing techniques that may be applied between the boundaries of the slices so as to generate a 3-D surface, such as surface 60. Other smoothing techniques may be used. Smoothing may be performed, for example, via the module 96.

At 106, Voxel editing occurs, in which the CT volume is converted to a grid of blocks in three dimensional space. At 108 (optional), connectivity occurs. At 110, surface generation occurs, for example utilizing the Marching Cubes computer graphics algorithm, which proceeds through the voxels, taking eight neighbor locations at a time (thus forming an imaginary cube), then determining the polygon (s) needed to represent the part of the isosurface that passes through the cube. The individual polygons are then fused into the desired surface.

Figure 10A:
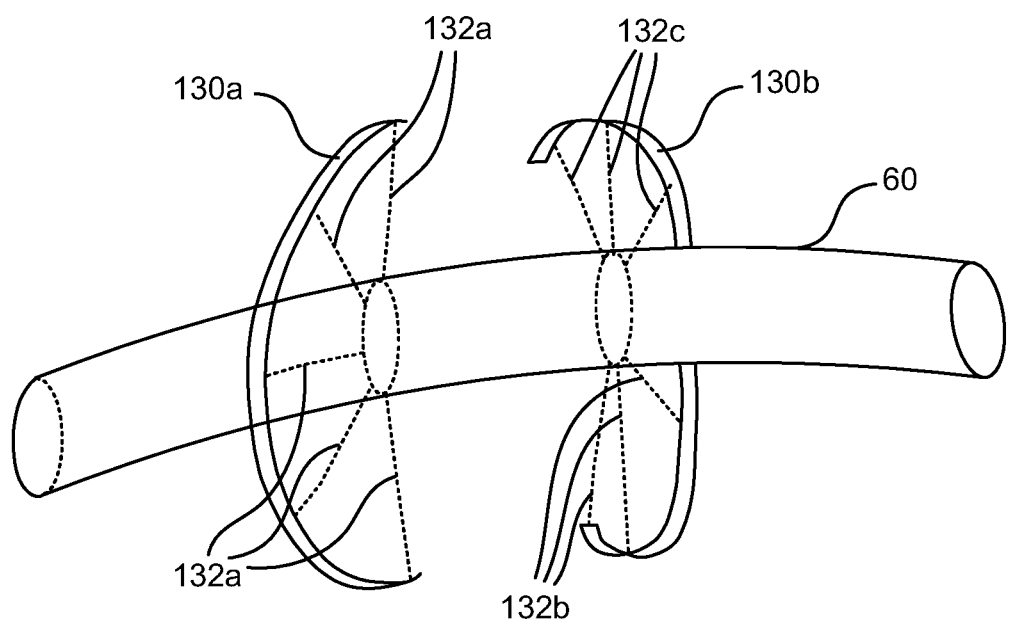
FIGS. 10A-10B depict a representation of three-dimensional surfaces for receiving input.

At 114, the desired surface is output, for example as shown as the surface 60 in FIG. 10A. For the example herein, the surface 60 represents a blood/tissue boundary of a blood vessel adjacent to a nerve of the renovascular system. The entire process in FIG. 8 may be automated using a segmentation scheme.

Figure 9:
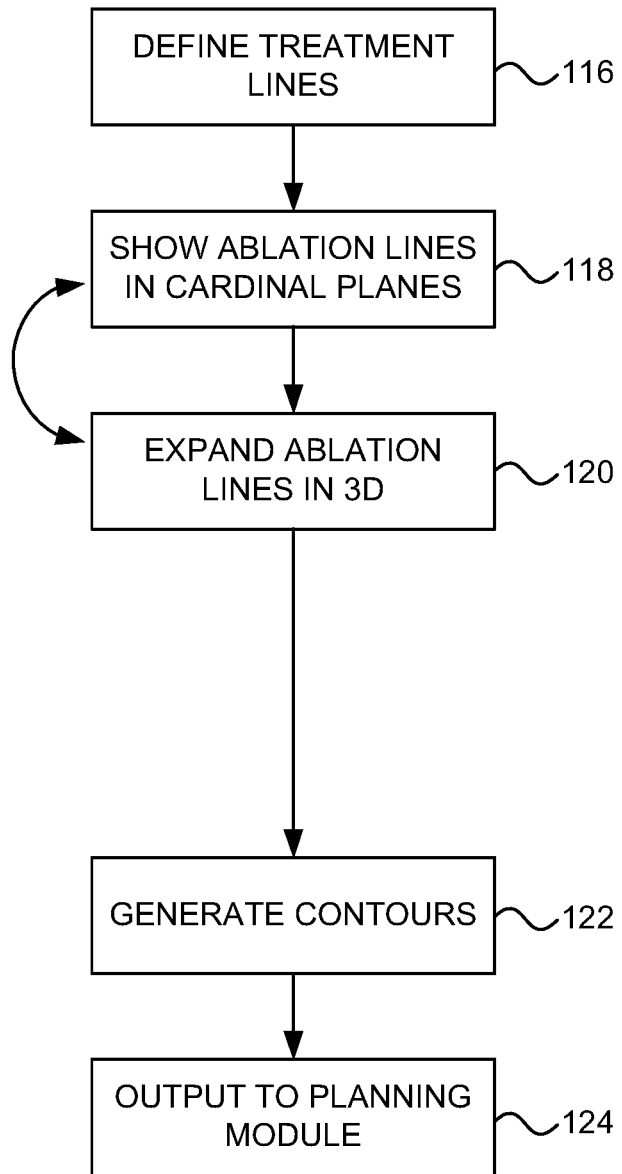
FIG. 9 is a flow chart representing a method for preparing a treatment plan utilizing the model of the surface generating in FIG. 8 in accordance with an embodiment.

FIG. 9 is a flow chart representing a method for preparing a treatment plan utilizing the surface 60 generated in FIG. 8. Beginning at 116, desired treatment pattern 130*a* and 130*b* (FIG. 10A) corresponding to a radiation target are received with reference to the surface 60. For renal neuromodulation the radiation target comprises the nerves adjacent to the blood vessel. The nerves are offset a distance from the blood/tissue boundary of the blood vessel. Thus the radiation target and desired treatment pattern lines 130*a* and 130*b* are offset a distance 132 from surface 60 so as to provide a neural function altering dose of radiation at the nerves and a safe luminal dose of radiation at the blood/vessel boundary. As shown in FIG. 10A, desired treatment pattern line 130*a* is offset distance fixed distance 132*a* from surface 60. However, treatment pattern line 130*b* is offset a different distance 132*b* and 132*c* from surface 60. Thus it should be understood that offset distance 132 may vary for desired treatment patterns 130 and may even vary for individual treatment patterns 130, e.g. treatment pattern 130*b* is offset a distance which varies from offset distance 132*b* and 132*c*.

Figure 10B:
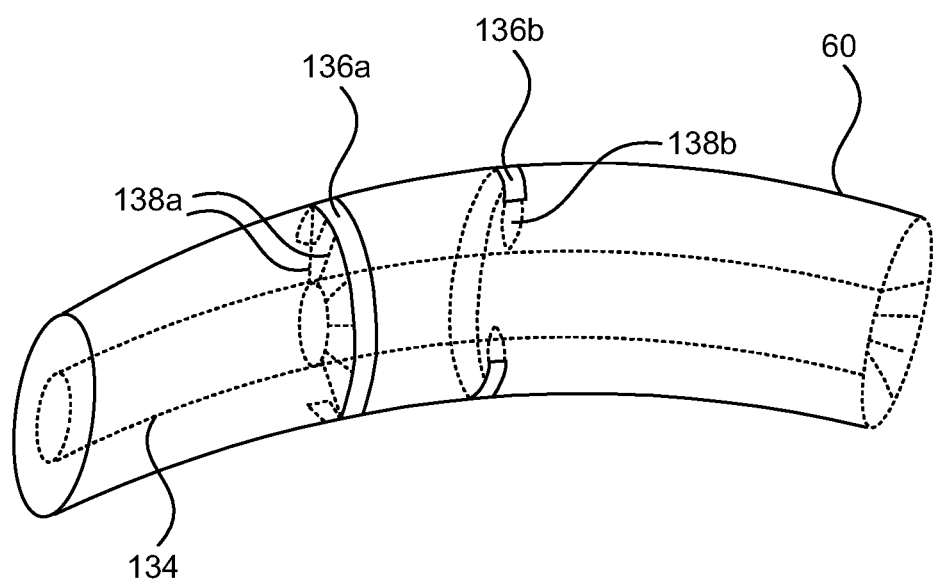

In the alternative embodiment shown in FIG. 10B, the treatment plan may be prepared utilizing a surface 60 which is offset a distance 138 from blood/vessel boundary surface 134. The offset distance 138 from the blood/vessel boundary may correspond to a location of the adjacent target nerves. Thus the offset surface 60 may correspond to an estimated location of the target nerves. The modeling module may identify the blood/vessel boundary surface 134 and surface 60 may be generated by offsetting a distance 138 from the blood/vessel boundary surface 134. Similar to above, the offset distance 138 may vary radially and longitudinally along the blood/vessel boundary 134. The desired treatment patterns 136a and 136b may then be received with reference to the surface 60. The treatment patterns 136 are similarly configured to provide a neural function altering dose of radiation at the adjacent nerve and a safe luminal dose of radiation at the blood/vessel boundary.

These desired treatment lines 130 may be snapped and extended at an offset distance 132 from the exterior of the surface 60. Alternatively, the desired treatment lines 136 may be snapped directly to and extended along the exterior of surface 60. For example a physician may utilize the user interface input device 80 to input a desired treatment pattern. In an example, a physician may click along the surface and the desired treatment pattern lines may extend as a straight line between clicks. In the embodiment in 10A, the desired treatment lines 130 extend at a desired offset distance from the surface. In the embodiment of 10B, the desired treatment lines 136 extend along the exterior of surface 60. Smoothing may be enabled. If desired, the surface 60 may be rotated, panned, and zoomed on the screen, or the pitch or yaw may be altered, so as to allow the physician to access a desired view of the surface to properly orient the treatment lines 130. Such manipulation features are known in existing 3-D modeling and display software.

Applying the treatment lines 130 and 136 via the user interface input device 80 allows the planning medical professional to input an appropriate treatment pattern as a series of lines or curves relative to the three dimensional model surface 60. The treatment lines 130 and 136 may be applied as a very thin line or as a thickness that is defined by the system or user. In accordance with an embodiment, the treatment lines are displayed at a width that is sufficient to reduce neural activity in across the treatment line. Using such a width provides intuitive visual feedback to a user of the system, so that the user may have a more realistic idea of the location and breadth of a lesion pattern.

Figure 11:
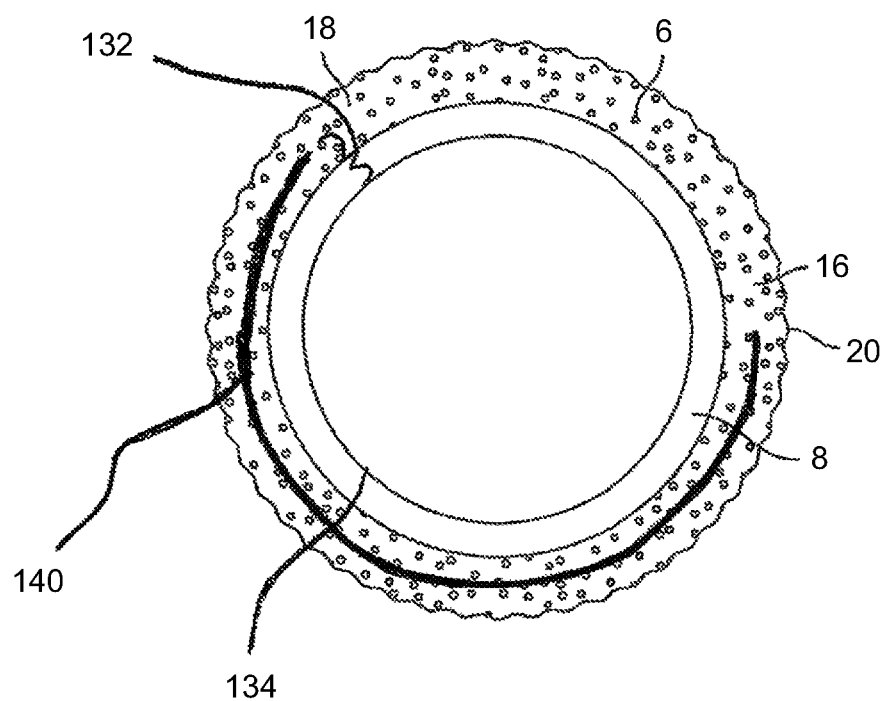
FIG. 11 is a representation of a cardinal plane of the blood vessel adjacent to the target nerves for which the surface of FIGS. 10A-10B has been generated, showing intersection points of the treatment lines of FIGS. 10A-10B.

If desired, at 118 the treatment lines may be shown in one or more cardinal planes. As an example, as is shown in FIG. 11, a cardinal plan of the renal artery 8 for which surface 60 was generated shows intersection line 140. The intersection line 140 represents the cross section of the treatment lines 130 and 136 at the given cardinal plane. As can be seen, the intersection line 140 is an offset distance 132 from the blood/vessel boundary surface 134. Further, the intersection line 140 is located within a region of the renal nerves 6. Other cardinal planes may be displayed either simultaneously on the display or by toggling between a view of the surface 60 and the cardinal plane. The cardinal planes may represent, for example, data from a single CT slice.

Figure 12A:
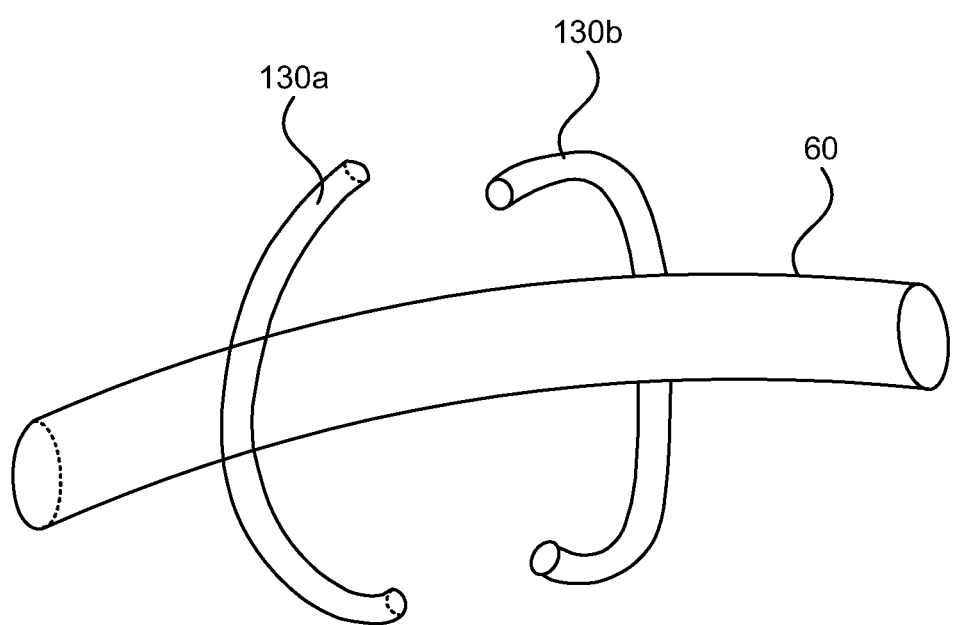
FIGS. 12A-12B is a representation of the expansion of the treatment lines in FIGS. 10A-10B into volumes in accordance with an embodiment.
Figure 12B:
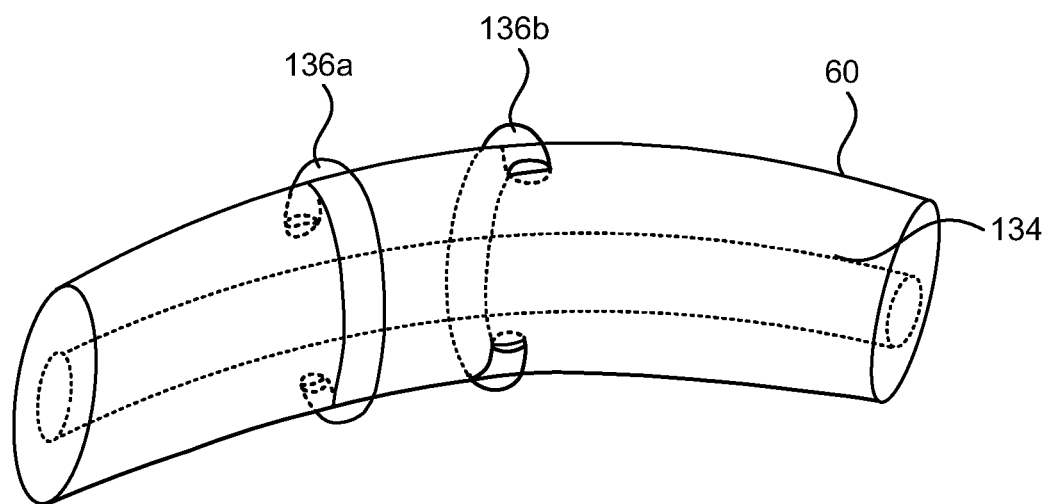
Figure 13:
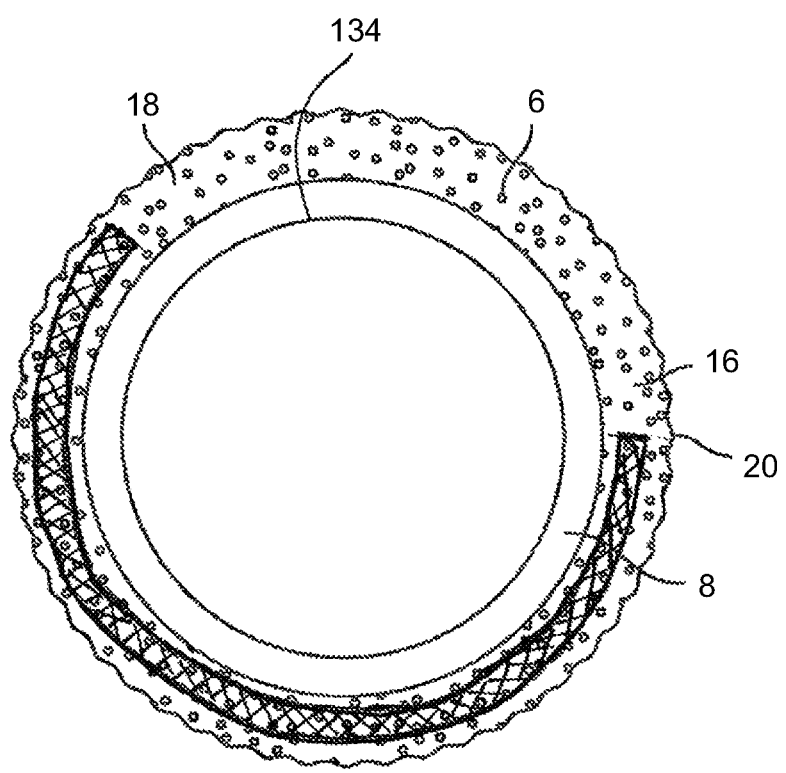
FIG. 13 is a representation of a cardinal plane of the blood vessel adjacent to the target nerves for which the surface of FIGS. 10A-10B has been generated, showing the intersection area of the volumes of FIGS. 12A-12B.

At 120, the desired treatment lines 130 and 136 are expanded to volumes so as to provide the desired therapeutic benefit at the adjacent nerves, and may be visualized on the display in three dimensions, FIGS. 12A-12B. 118 may occur after 120 and indeed, unless stated otherwise herein, the acts set forth in the flowcharts of this disclosure are not limited to the order in which they are presented. To visualize the volume in three dimensions, the treatment lines 130 and 136 may be given a three dimensional thickness by generating loops having a radius around the treatment pattern lines 130 and 136. Since the offset distance corresponds to a distance from the blood/vessel boundary surface, the radius should be less than the offset distance so as to provide a neural function altering dose of radiation at the target and a safe luminal dose of radiation at the blood/vessel boundary. The radius may be applied around the treatment pattern lines, or separate width and length radii may be used. In an example, volumes may be generated utilizing a radius of 0.5 mm, but other radii may be used. The expansion of intersection line 140 (FIG. 11) to a volume is depicted in the cardinal plane in FIG. 13. FIG. 13 shows the cardinal plane of the blood vessel adjacent to the target nerves. The expansion of intersection line 140 (FIG. 11) to a treatment volume creates an intersection area 141 indicative of the treatment volume intersection at this cardinal plane.

In an embodiment the volumes enclose a portion of the nerves adjacent to the blood vessel and define a planning target volume (PTV) for treatment planning purposes. The PTV represents the area of tissue of interest at which treatment is desirably to occur. In the example of the renal artery, the PTV is preferably a portion of the renal plexus, and may comprise one or more annular circumferential segments. The PTV should also be limited at the blood/vessel boundary surface 134 so as to provide a safe luminal dose of radiation at the blood/vessel boundary to inhibit hyperplasia.

Figure 14:
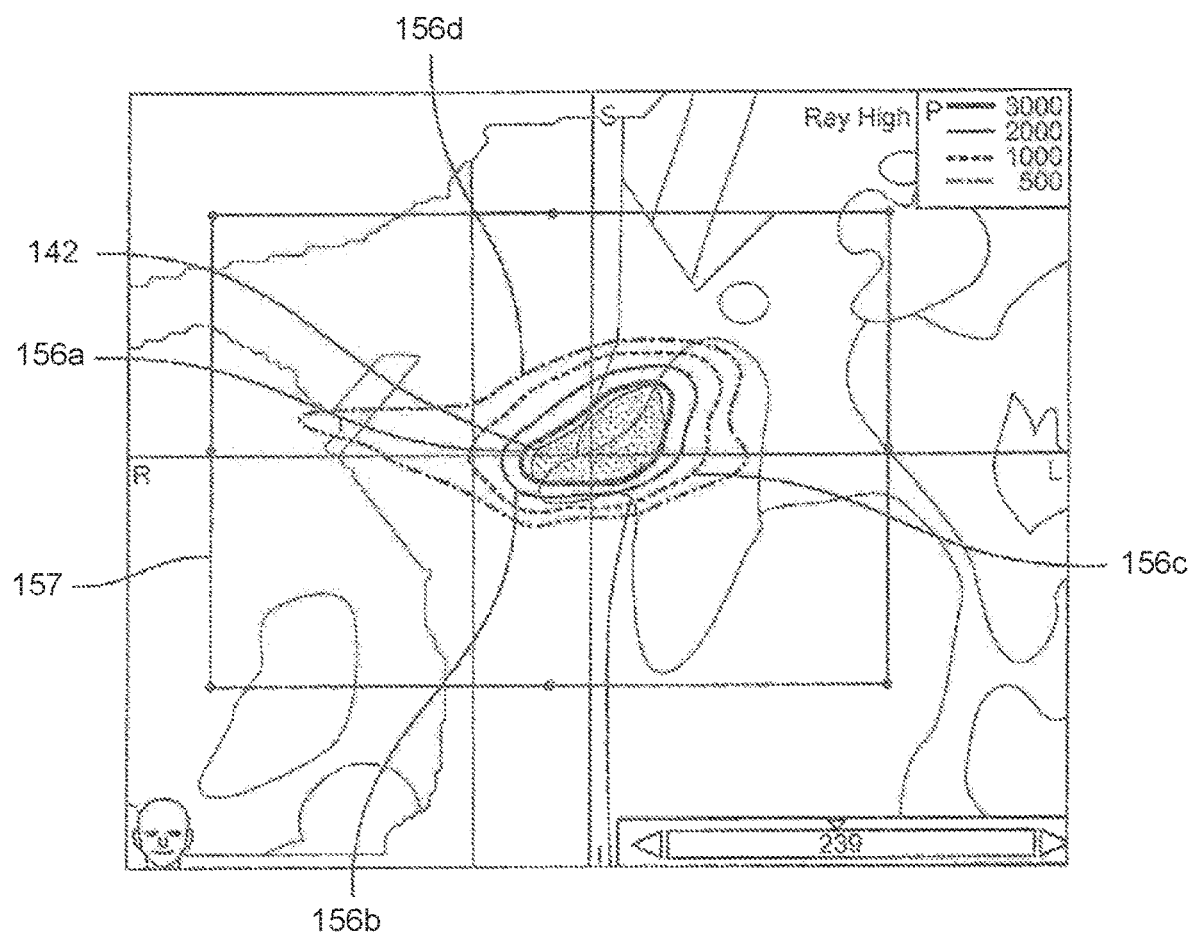
FIG. 14 is an axial slice of a portion of the renovascular system with a planning target volume projected thereon in accordance with an embodiment.

At 122, the PTV is scan converted to generate contours in each of the cardinal planes. Existing radiosurgical radiation beam calculating modules may be used to determine the resulting radiation contour distribution. Existing radiosurgical planning approaches for identification of radiation sensitive structures may be implemented. The input to such existing calculating modules may require input via slices, such as conventional CT slices. Thus, if such calculating modules are used, the CT slices are utilized to generate the solid volume (FIG. 8), the plan is formed on the solid volume (FIG. 9), and then the plan at each slice is provided back to the calculating module to generate the contours. Thus, the output 124 may be an output relative to each of the original CT slices. An example of an axial slice of the contours 142 is shown in FIG. 14.

Alternatively, the treatment pattern lines 130 or 136 may be defined using a cardiac and/or respiratory gated 4DCT data set. Suppose there N (typically N=10) volumes of CT data acquired over time. A blood/vessel surface (e.g., the surface 60) will be constructed from each CT volume, resulting in N such surfaces. Using each surface, a set of treatment lines will be defined by the user, resulting in N such treatment lines. This time-varying treatment lines and the time-varying CT data will then be imported to a treatment planning station line treatment planning module, e.g., MULTIPLAN, for generating a treatment plan. Alternatively, one treatment pattern line set, whose volume will include the volumes from all individual treatment pattern lines, can be generated and used for planning.

In accordance with an embodiment, placement of the treatment pattern lines on a surface may be partially or fully automated. A template of possible treatment pattern lines may be provided to the user, and the user may then drag and drop the selected template at a proper location on the surface. The user may modify the treatment line locally by moving it around on the surface. The thickness may also be changed.

The contours 142 may be saved, for example, as DICOM RTSS (Radiation Therapy Structure Sets) files. The planner to which they are output may be, for example, MULTIPLAN. In an embodiment, evaluation is done using PTV. Optimizing the plan based on the PTV is preferred because focus is on the actual area in which treatment is desired.

In another embodiment, instead of transmitting the treatment pattern lines as 2D contours in cardinal planes or oblique planes to a planning module, the treatment pattern lines may be transmitted as 3D shapes to the planning module.

Figure 15:
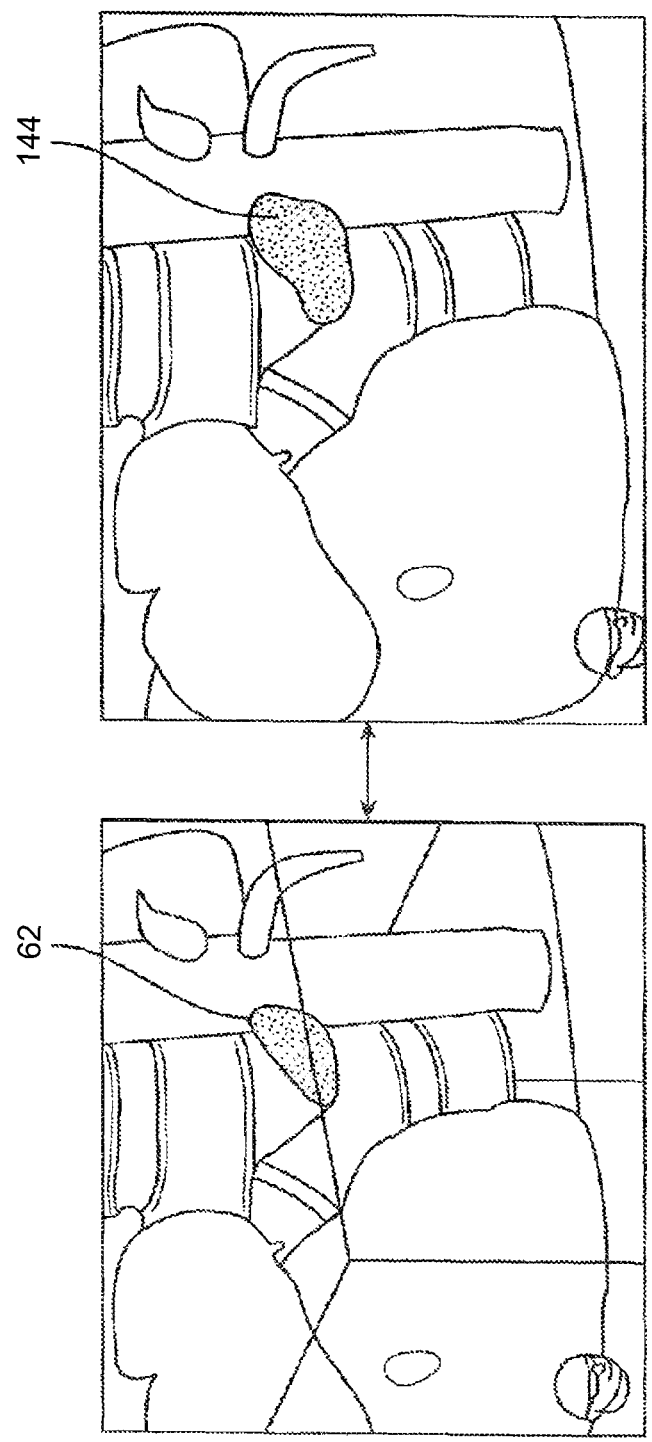
FIG. 15 is a representation of a three dimensional model of a portion of the renovascular system, with a treatment plan added on a left view and a dose cloud added on a right view, in accordance with embodiments herein.

Along with inputting a desired treatment pattern 62, as schematically illustrated in FIG. 5A, the planning module and user interface will preferably output an estimate of the actual radiation exposure relative to the blood/vessel surface, preferably in the form of an estimated tissue exposure 144 (FIG. 15). Estimated exposure 144 may represent the portion of tissue relative to surface 60 which receives a radiation dose above a necrotic threshold, optionally based on radiation beams and radiation dose output from an existing radiosurgical treatment planner. Alternative patterns may represent an estimate of tissue which will receive a sufficient dose of radiation for therapeutic remodeling so as to reduce the sympathetic activity of the adjacent nerve. The user may interactively develop the plan based on iterative input into and output from the planning treatment module 102.

Figure 16:
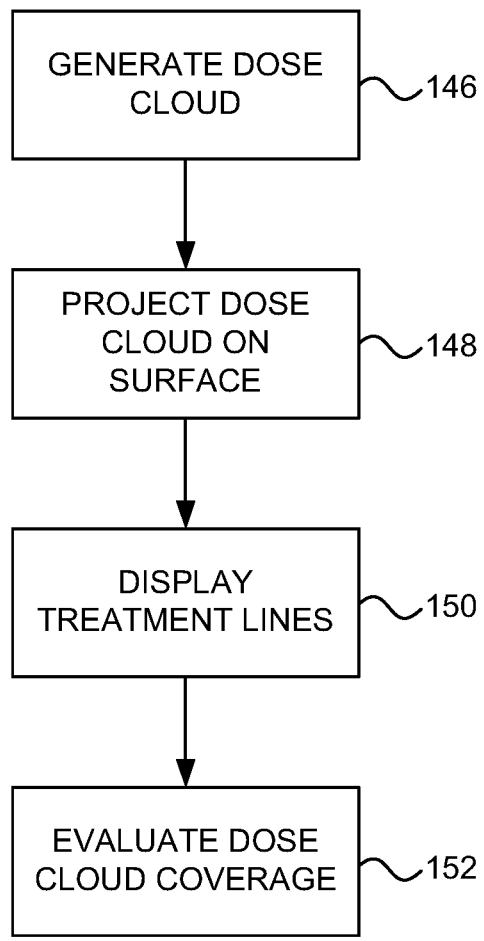
FIG. 16 is a flow chart representing a method of evaluating a dose cloud with respect to the blood/vessel boundary surface in accordance with an embodiment.

Ideally, the dose cloud should correspond to the treatment lines. FIG. 16 is a flow chart representing a method of evaluating a dose cloud with respect to the generated surface 60 in accordance with an embodiment. At 146, the dose cloud is generated and is overlaid relative to the surface 60 at 148. If desired, the treatment lines 130 or 136 are displayed relative to the surface 60 at 150.

Figure 17:
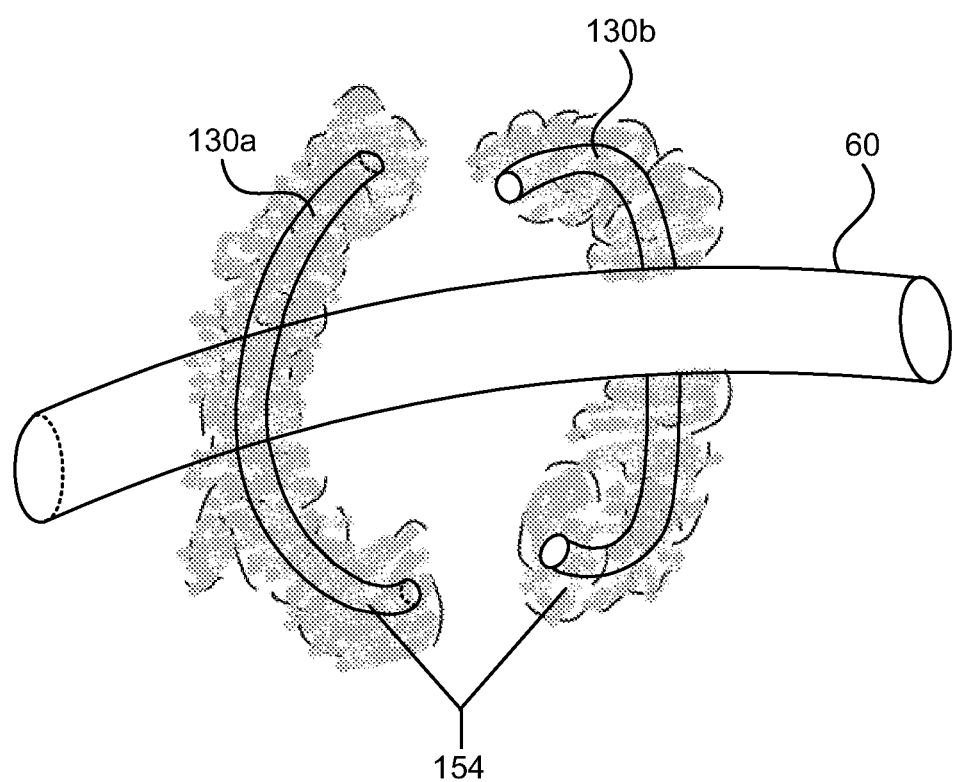
FIG. 17 shows a dose cloud projected relative to the generated surface along with the treatment lines in accordance with an embodiment.
Figure 18D:
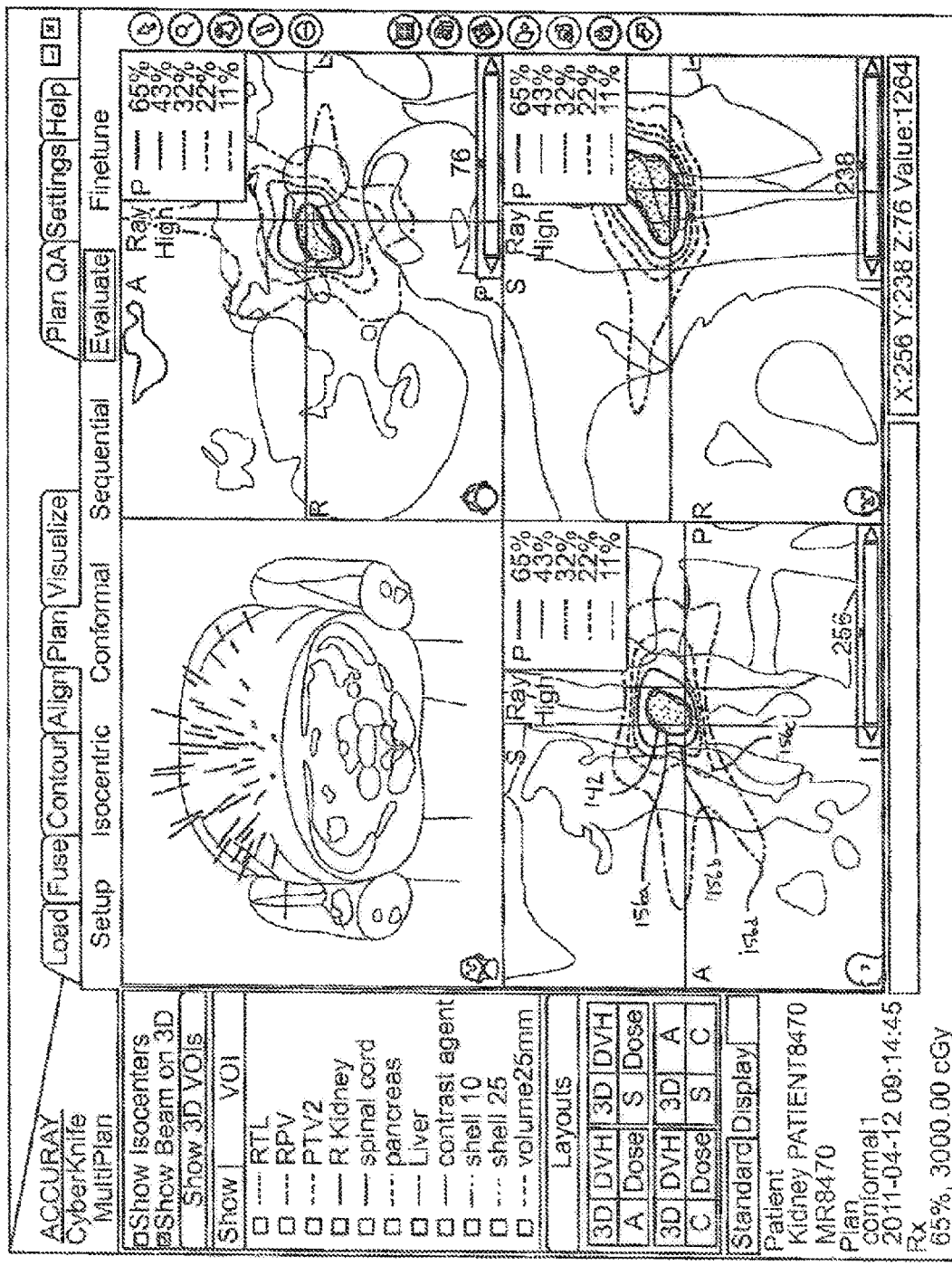
Figure 18E:
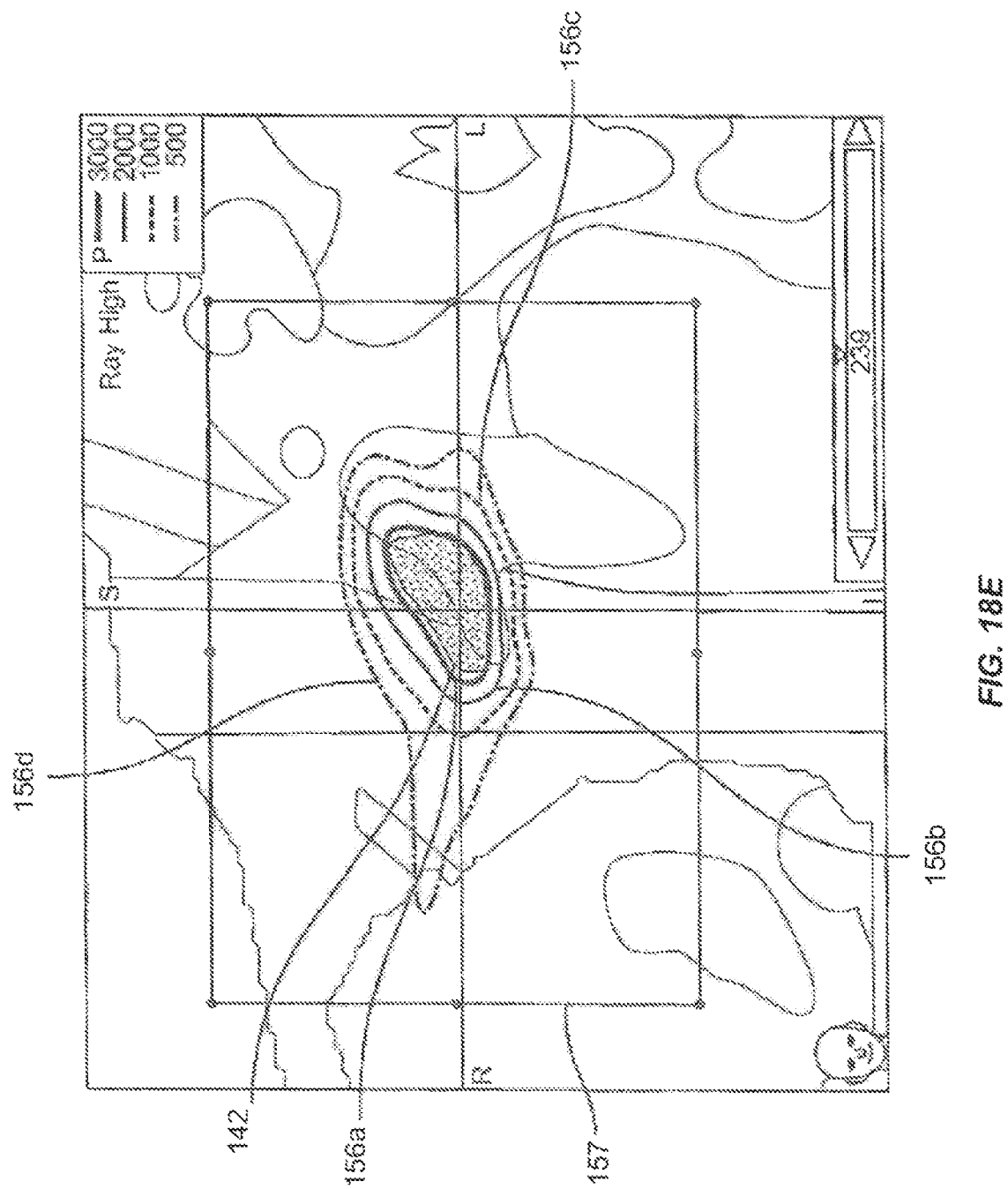

As shown in FIG. 17, displaying the treatment lines 130 and a dose cloud 154 relative to the surface 60 allows a visual inspection of whether the dose cloud is covering the target intended by the physician. To this end, at 152, the physician may visually evaluate whether the dose cloud is covering the target. As can be seen in FIG. 17, for at least the view shown in the drawing, the dose cloud 154 provides a safe radiation luminal dose of radiation at the blood/vessel boundary. Rotation, panning, or zooming of the surface, or adjustment of the pitch and/or yaw, may be required for a full inspection of dosage coverage.

The dose cloud 154 may represent, for example, all dose values that are greater than a particular threshold or, as an alternative, dose values lying in a range between a minimum and a maximum. If desired, as shown in FIG. 18A-18E, an axial slice of each cardinal plane may be provided, with the isodose lines 156 and inner most contour 142 shown thereon. This representation permits a physician to look at each slice to ensure that the dose is covering (e.g., surrounding) the target adequately while the blood/vessel boundary receives a safe luminal dose of radiation. Starting in order from the innermost to the outermost isodose line, after the contours corresponding to target 142, the points on the innermost isodose 156a correspond to an absorbed dose of 30 Gy of radiation, and the points inside of isodose 156a receive an absorbed dose of at least 30 Gy of radiation. The points on the next innermost isodose 156b correspond to an absorbed dose of 20 Gy of radiation, and the points inside of isodose 156b receive an absorbed dose of at least 20 Gy of radiation. The points on the next innermost isodose 156c correspond to an absorbed dose of 10 Gy of radiation, and the points inside of isodose 156c receive an absorbed dose of at least 10 Gy of radiation. The points on outer isodose 156d correspond to an absorbed dose of 5 Gy of radiation, and the points inside of isodose 156d receive an absorbed dose of at least 5 Gy of radiation. It is noted that points within box 157 receive less than 5 Gy of radiation. However, it is noted that there may be areas outside a given isodose/box 157 and/or inside a given isodose/box 157 where the predicted absorbed dose is different than specified. By way of example, there may be areas near the skin that experience a dose flare and/or areas inside the isodose lines that experience a dose deficiency. The size of the elements of these figures is scaled to the anatomy of an average male adult. Along these lines, it can be seen that embodiments of the present invention result in inhomogeneous radiation delivery that delivers more than about 15 Gy within 4 mm of the outer wall of the renal arteries. It is noted that while a unilateral treatment has been depicted with respect to FIGS. 18A-18E, the data presented with respect to these figures is applicable to a bilateral treatment as well, and the opposite renovascular structure from that depicted in the FIGS. would substantially correspond to that depicted in the FIGS.

Figure 19:
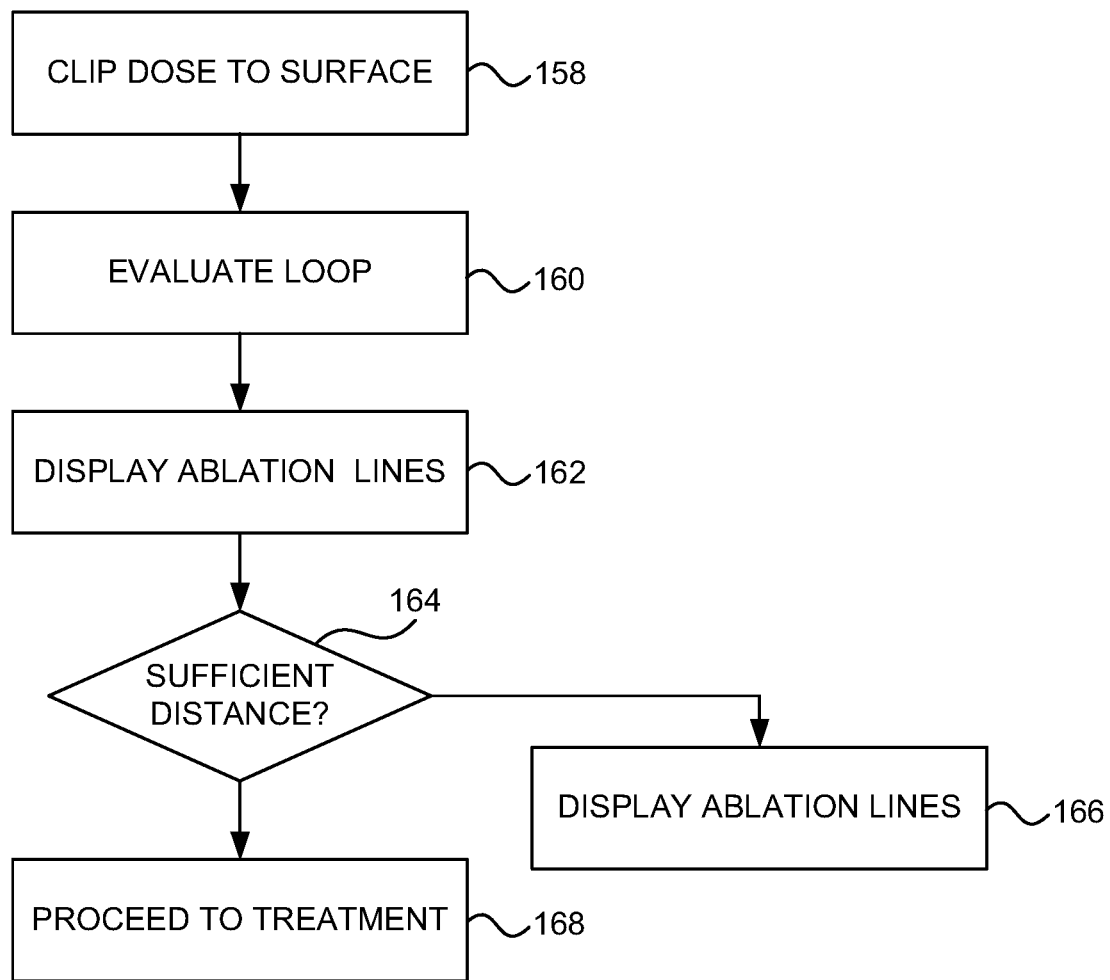
FIG. 19 is a flow chart representing a method of determining if a dose cloud is acceptable in accordance with an embodiment.
Figure 20:
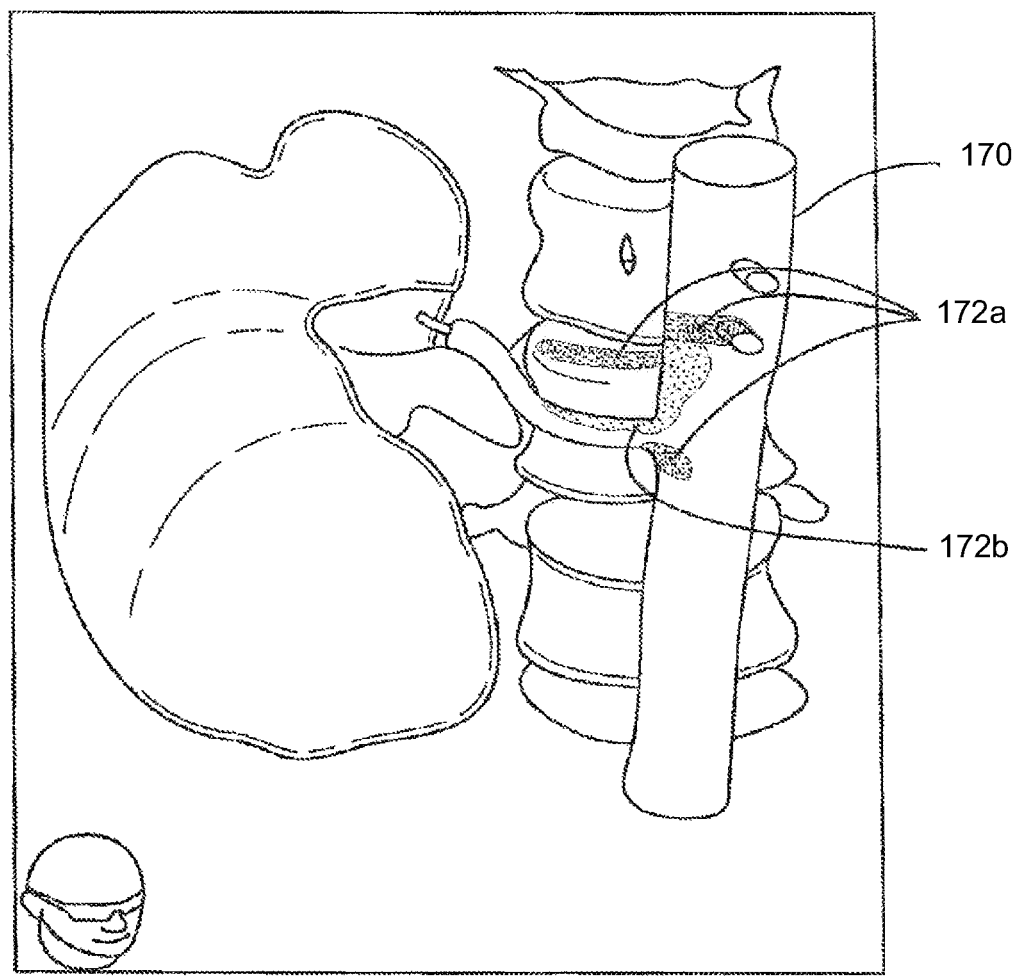
FIG. 20 shows a surface patch indicating radiation dosage coverage on a generated tissue surface in accordance with an embodiment.

FIG. 19 is a flow chart representing a method of determining if a dose is sufficient in accordance with an alternate embodiment. The method in FIG. 19 involves clipping a dose cloud relative to a surface 170 (FIG. 20), and may be used in addition to, or instead of the visual inspection described above, where the dose cloud is represented more as a contour. At 158, the region corresponding to the acceptable dose value is clipped relative to a surface 170. The dose values may be represented in isodose fashion, with different doses being displayed in different ways, for example as different colors. Alternatively, as in the previous embodiment, all doses exceeding a value or falling in a range may be displayed.

By clipping the dose value relative to a surface, the dose is presented as a curved surface patches 172a and 172b (FIG. 20) on the surface 170. A physician may visually evaluate the surface patch 172a with respect to the target tissue to determine whether the target tissue receives a neural function altering dose of radiation while the adjacent tissue is exposed to acceptable doses of radiation 172b. For example, the surface patch 172a may be evaluated to determine whether it is wide enough to reduce neural activity in the tissues being treated.

In addition, the physician may evaluate the surface patch 172a to determine whether the surface patch 172a provides a safe luminal dose of radiation at the blood/vessel boundary surface at 160. If there are any radiation doses at the blood/tissue boundary surface which could prompt hyperplasia or within the blood vessel walls which could occlude the blood in the blood vessel, a reduction in hypertension may not be provided by the radiological treatment. To this end, at 162, the physician evaluates whether the surface patch 172a is offset a sufficient distance from the blood/tissue boundary surface, such that hyperplasia and blood occlusion may be inhibited. If not, an error may be generated at 164 either by software or a recognition by the user, causing the physician to construct a new plan or causing the computer system 68 to generate an error message, or to be handled in another manner. If the surface patch 172a is a sufficient offset distance from the blood/tissue boundary surface, then the physician may proceed to treatment at 168.

The physician and/or the computer system 68 may rotate and otherwise manipulate the surface 170 so that the physician may fully inspect the surface patch 172a. In an alternate embodiment, software may walk across the surface patch 172a to confirm that the surface patch remains a certain offset distance from the blood/tissue boundary surface. This same software or visual inspection may be used to determine whether the surface patch 172a is sufficiently wide to reduce neural activity in the adjacent nerves. For example, the software may crawl around the surface 172a and evaluate a pixel width of the surface patch 172a. If the pixel width falls below a threshold, an error may be generated.

Any effects of possible misalignment errors (x, y, z translation and roll, pitch, yaw, rotation errors) during treatment may be evaluated with this system. The surface 170 or the CT data set may be translated and rotated in relation to the dose cloud to understand the effect of any misalignment on the necessary offset distance between the radiation dose and the blood/vessel boundary surface. Alternatively the dose cloud may be translated or rotated in relation to the surface or the CT data set.

After the contours are approved, the plan 26 is complete, and may be implemented. Radiosurgical treatment of the nerves may be initiated, for example, by positioning the patient on patient support 44, bringing the patient into alignment with robot arm 34, and directing the planned series of radiation beams from the linear accelerator 32 to the target region of the renovascular system.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

We claim:

1. A radiosurgical method for altering a neural function of a patient body, the radiosurgical method comprising:

acquiring image data from a blood vessel adjacent to a nerve;

generating a three-dimensional model by identifying a boundary between the blood vessel and blood flowing therein from the image data;

receiving an input regarding a radiation target with a reference to an image of the three-dimensional model, wherein the radiation target is offset from a surface of the boundary between the blood vessel and the blood flowing therein;

generating an ionizing radiation treatment plan based upon the input regarding the radiation target; and projecting a dose cloud to the three-dimensional model based upon the ionizing radiation treatment plan;

wherein the image data comprises a time sequence spanning one or more movement cycles of a patient body.

2. The radiosurgical method of claim 1, wherein the input regarding the radiation target comprises one or more treatment lines applied through a user interface input device.

3. The radiosurgical method of claim 1, wherein the input regarding the radiation target comprises one or more treatment lines that are expanded to volumes and displayed in the three-dimensional model.

4. The radiosurgical method of claim 1, wherein the dose cloud comprises an estimate of an actual radiation exposure of a body tissue.

5. The radiosurgical method of claim 1, further comprising evaluating the ionizing radiation treatment plan based on the dose cloud and revising the ionizing radiation treatment plan if the dose cloud does not cover the radiation target.

6. The radiosurgical method of claim 1, wherein the dose cloud comprises isodose lines corresponding to a predetermined dose of radiation.

7. The radiosurgical method of claim 1, further comprising evaluating the ionizing radiation treatment plan based on the dose cloud and generating an error message if the dose cloud is less than a predetermined distance from the boundary between the blood vessel and the blood flowing therein.

8. A radiosurgical system for altering a neural function of a patient body, the radiosurgical system comprising:

a computing device that includes at least one processor and a storage subsystem, the computing device configured to:

acquire image data of a blood vessel adjacent to a nerve, the image data obtained by an imaging modality;

generate a three-dimensional model by identifying a boundary between the blood vessel and blood flowing therein from the image data;

receive an input regarding a radiation target with a reference to an image of the three-dimensional model, wherein the radiation target is offset from a surface of the boundary between the blood vessel and the blood flowing therein;

generate an ionizing radiation treatment plan based upon the input regarding the radiation target; and project a dose cloud to the three-dimensional model based upon the ionizing radiation treatment plan;

wherein the image data comprises a time sequence spanning one or more movement cycles of a patient body.

9. The radiosurgical system of claim 8, wherein the input regarding the radiation target comprises one or more treatment lines applied through a user interface input device.

10. The radiosurgical system of claim 8, wherein the input regarding the radiation target comprises one or more treatment lines that are expanded to volumes and displayed in the three-dimensional model.

11. The radiosurgical system of claim 8, wherein the dose cloud comprises an estimate of an actual radiation exposure of a body tissue.

12. The radiosurgical system of claim 8, wherein the computing device is further configured to evaluate the ionizing radiation treatment plan based on the dose cloud and revise the ionizing radiation treatment plan if the dose cloud does not cover the radiation target.

13. The radiosurgical system of claim 8, wherein the dose cloud comprises isodose lines corresponding to a predetermined dose of radiation.

14. The radiosurgical system of claim 8, wherein the computing device is further configured to evaluate the ionizing radiation treatment plan based on the dose cloud and generate an error message if the dose cloud is less than a predetermined distance from the boundary between the blood vessel and the blood flowing therein.

15. A non-transitory computer-readable medium with computer-executable instructions stored thereon that, when executed by a processor, cause the processor to:

acquire image data from a blood vessel adjacent to a nerve;

generate a three-dimensional model by identifying a boundary between the blood vessel and blood flowing therein from the image data;

receive an input regarding a radiation target with a reference to an image of the three-dimensional model, wherein the radiation target is offset from a surface of the boundary between the blood vessel and the blood flowing therein;

generate an ionizing radiation treatment plan based upon the input regarding the radiation target; and project a dose cloud to the three-dimensional model based upon the ionizing radiation treatment plan;

wherein the image data comprises a time sequence spanning one or more movement cycles of a patient body.

16. The non-transitory computer-readable medium of claim 15, wherein the input regarding the radiation target comprises one or more treatment lines applied through a user interface input device.

17. The non-transitory computer-readable medium of claim 15, wherein the input regarding the radiation target comprises one or more treatment lines that are expanded to volumes and displayed in the three-dimensional model.

\* \* \* \* \*